(12) United States Patent
Fu et al.

(10) Patent No.: US 12,693,249 B2
(45) Date of Patent: Jul. 28, 2026

(54) METHOD FOR QUANTITATIVE EVALUATION ON SENSITIVITY OF SHALE OIL AND GAS RESERVOIR TO INJECTED FLUIDS

(71) Applicant: Northeast Petroleum University, Daqing City (CN)

(72) Inventors: Xiaofei Fu, Daqing (CN); Jianguang Wei, Daqing (CN); Xiaofeng Zhou, Daqing (CN); Anlun Wang, Daqing (CN); Xiaoqing Zhao, Daqing (CN); Binhui Li, Daqing (CN); Ying Yang, Daqing (CN); Rui Wang, Daqing (CN); Jiangtao Li, Daqing (CN); Lidong Zhao, Daqing (CN)

(73) Assignee: Northeast Petroleum University, Daqing City (CN)

( * ) Notice: Subject to any disclaimer, the term of this patent is extended or adjusted under 35 U.S.C. 154(b) by 454 days.

(21) Appl. No.: 18/353,553

(22) Filed: Jul. 17, 2023

(65) Prior Publication Data

US 2024/0027379 A1 Jan. 25, 2024

(30) Foreign Application Priority Data

Jul. 19, 2022 (CN) ......................... 202210845363.X

(51) Int. Cl.
*G01N 24/08* (2006.01)
*G01N 1/34* (2006.01)
(Continued)

(52) U.S. Cl.
CPC ............. *G01N 24/081* (2013.01); *G01N 1/34* (2013.01); *G01N 1/44* (2013.01); *G01N 5/04* (2013.01);
(Continued)

(58) Field of Classification Search
CPC .... G01N 24/081; G01N 15/088; G01N 33/24; G01N 15/08; G01N 24/082; G01N 1/44;
(Continued)

(56) References Cited

U.S. PATENT DOCUMENTS

2017/0030819 A1* 2/2017 Mccarty ................. E21B 43/26
2019/0178824 A1* 6/2019 Kwak ................. G01N 24/081
(Continued)

FOREIGN PATENT DOCUMENTS

CN 104990851 A * 10/2015

*Primary Examiner* — Catherine T. Rastovski
*Assistant Examiner* — Carter W Ferrell
(74) *Attorney, Agent, or Firm* — Adam K Sacharoff; Much Shelist, PC

(57) ABSTRACT

The present disclosure provides a method for quantitative evaluation on a sensitivity of a shale oil and gas reservoir to injected fluids. The method includes the following steps: (I) preparation of rock samples; (II) quantitative evaluation on sensitivities of a shale porosity and a bedding fracture permeability to an injected fluid; and (III) quantitative evaluation on a sensitivity of a shale matrix permeability to an injected fluid. A method for comprehensive evaluation on a sensitivity of a shale oil and gas reservoir to injected fluids is innovatively provided based on the nuclear magnetic resonance testing technology with two basic physical property parameters: porosity and permeability. The method realizes quantitative evaluation on sensitivities of pores of different sizes and matrix of shale and a bedding fracture permeability to injected fluids, and realizes quantitative and accurate evaluation on a sensitivity of a shale oil and gas reservoir to injected fluids.

3 Claims, 9 Drawing Sheets

(51) Int. Cl.

| | |
|---|---|
| *G01N 1/44* | (2006.01) |
| *G01N 5/04* | (2006.01) |
| *G01N 15/08* | (2006.01) |
| *G01N 33/24* | (2006.01) |

(52) U.S. Cl.
CPC ....... *G01N 15/082* (2013.01); *G01N 15/0886* (2013.01); *G01N 33/24* (2013.01)

(58) Field of Classification Search
CPC ........ G01N 1/34; G01N 15/082; G01N 24/08; G01N 5/04; G01N 15/0886; G01R 33/448; G01V 3/32; E21B 49/00; Y02A 90/30

See application file for complete search history.

(56) References Cited

U.S. PATENT DOCUMENTS

2020/0173902 A1* 6/2020 Wang ..................... G01N 15/08
2021/0072171 A1* 3/2021 Kuang ................. G01R 33/448

* cited by examiner

1#

2#

3#

4#

5#

6#

METHOD FOR QUANTITATIVE EVALUATION ON SENSITIVITY OF SHALE OIL AND GAS RESERVOIR TO INJECTED FLUIDS

CROSS REFERENCE TO RELATED APPLICATION

This patent application claims the benefit and priority of Chinese Patent Application No. 202210845363.X, filed with the China National Intellectual Property Administration on Jul. 19, 2022, the disclosure of which is incorporated by reference herein in its entirety as part of the present application.

TECHNICAL FIELD

The present disclosure relates to the field of exploration and development of unconventional shale oil and gas reservoirs, and in particular, to a method for evaluation on a sensitivity of a shale oil and gas reservoir to injected fluids.

BACKGROUND

As the exploration and development techniques for oil and gas resources have become increasingly mature in China, lower limits of physical properties of oil and gas reservoirs gradually are gradually drawn close to those of unconventional oil and gas resources. Unconventional oil and gas resources such as shale oil and gas exhibit a huge development potential and are gradually becoming important replaced strategic resources in China. At present, a mode of hydraulic fracturing in horizontal wells is generally adopted in combination with a depletion exploitation way to realize effective development of unconventional shale oil and gas resources at home and abroad. A fluid needs to be injected in a large volume during the fracturing of a shale oil and gas reservoir. Degrees of damage or improvement of different types of injected fluids to the pore structure and the permeability of a shale reservoir need to be quantitatively evaluated. Therefore, it is necessary to systematically carry out research on quantitative evaluation of sensitivity of a shale oil and gas reservoir to injected fluids.

At present, existing methods for quantitative evaluation on a sensitivity of a reservoir to injected fluids mainly follow standard SY/T 5358-2010 "Formation damage evaluation by flow test". The measurement principle of the standard is as follows: based on the traditional Darcy's law, the sensitivity of a reservoir is evaluated by measuring a relative change rate of permeabilities of a rock sample before and after contacting with an injected fluid by a displacement method.

Shale oil and gas reservoirs are super tight oil and gas reservoirs with a lot of micro-nano pores developing therein and have a matrix permeability far below that of a conventional sandstone reservoir. With the standard SY/T 5358-2010 "Formation damage evaluation by flow test", quantitative evaluation on a sensitivity of a shale oil and gas reservoir to injected fluids cannot be realized mainly for the following reasons.

(1) An effective driving system cannot be established for a shale rock sample. During an experiment, if the driving system is established with a high differential pressure, a confining pressure of a large value needs to be applied to the rock sample. Due to great brittleness of the shale rock sample, the rock sample is probe to cracking under the action of the confining pressure of a large value, which in turn affects the accuracy of experimental measurement. (2)

Due to extremely low shale matrix and bedding fracture permeabilities, it needs to take a long time to achieve stable flow and experimental data such as a differential pressure and a flow velocity needs to be manually recorded during measurement with a relatively large error. (3) The existing standard SY/T 5358-2010 "Formation damage evaluation by flow test" has only a single evaluation indicator because the sensitivity of a reservoir to an injected fluid is evaluated merely by measuring a relative change in the permeability of a rock sample before and after the injected fluid acts.

In view of the three technical disadvantages of the existing standard, it is necessary to establish a method suitable for quantitative evaluation on a sensitivity of a shale oil and gas reservoir. The present disclosure provides a method for evaluation on a sensitivity of a shale oil and gas reservoir to injected fluids based on the nuclear magnetic resonance technology with two basic physical property parameters: porosity and permeability. The method realizes comprehensive and accurate evaluation on sensitivities of super tight shale oil and gas reservoirs to injected fluids and provides a brand-new scientific means for quantitative evaluation on sensitivities of the shale oil and gas reservoirs to the injected fluids.

SUMMARY

To solve the problems in the background art, the present disclosure provides a method for evaluation on a sensitivity of a shale oil and gas reservoir to injected fluids. The present disclosure innovatively provides a method for comprehensive evaluation on a sensitivity of a shale oil and gas reservoir to injected fluids based on the nuclear magnetic resonance testing technology with two basic physical property parameters: porosity and permeability. The method realizes quantitative evaluation on sensitivities of pores of different sizes and matrix of shale and a bedding fracture permeability to injected fluids, solves the problems of the existing standard SY/T 5358-2010 "Formation damage evaluation by flow test", such as the failure to establish an effective driving system for a shale rock sample, a large experimental measurement error and a single evaluation indicator, and realizes quantitative and accurate evaluation on a sensitivity of a shale oil and gas reservoir to injected fluids.

The present disclosure adopts the following technical solutions: a method for quantitative evaluation on a sensitivity of a shale oil and gas reservoir to injected fluids, including the following steps:

(I) Preparation of Rock Samples selecting three shale rock samples from a same coring interval and marking the three shale rock samples as 1 #, 2 # and 3 #, where the rock samples 1 # and 2 # are used for determining a target drying temperature and time, and the rock sample 3 # is used for completing an evaluation experiment on sensitivities of a porosity and a permeability to an injected fluid; requirements for the shale rock sample 3 # are as follows: the rock sample is a standard plunger sample having a diameter of 2.5 cm and a length of greater than or equal to 5 cm; the rock sample 3 # is subjected to pretreatment before the experiment, and is cut into three small rock samples numbered as 4 #, 5 # and 6 #; the rock sample 4 # is used for a high pressure hg injection test; the rock sample 5 # is used for an evaluation experiment on sensitivities of a shale porosity and a bedding fracture permeability to an injected fluid; and the rock sample 6 is ground into 10/20-mesh particles for an evaluation experiment on a sensitivity of a shale matrix permeability;

(II) Quantitative Evaluation on Sensitivities of a Shale Porosity and a Bedding Fracture Permeability to an Injected Fluid where a process of quantitative evaluation on sensitivities of a shale porosity and a bedding fracture permeability to an injected fluid includes the following three steps:

A, determination of a target drying temperature and time of a shale rock sample before conducting the evaluation experiment on sensitivities of a shale porosity and a bedding fracture permeability to an injected fluid, removing mobile fluids including hydrocarbons and water existing in the rock samples to guarantee that the rock samples are clean;

(1) selecting two shale rock samples from a same coring interval and marking the shale rock samples as 1 # and 2 #;

(2) setting 10 different drying temperatures $T_{t1}$, $T_2$, $T_{t3}$, $T_{t4}$, $T_{t5}$, $T_{t6}$, $T_{t7}$, $T_{t8}$, $T_{t9}$ and $T_{t10}$, which progressively increase in sequence by 20° C.;

(3) drying the shale rock sample 1 # at a set temperature condition for to h, measuring corresponding rock sample masses $m_1$, $m_2$, $m_3$, $m_4$, $m_5$, $m_6$, $m_7$, $m_8$, $m_9$ and $m_{10}$ of the shale rock sample 1 # under different drying temperature conditions and carrying out a two-dimensional nuclear magnetic resonance test of the dried shale;

(4) plotting a changing curve of the mass of the shale rock sample 1 # with the drying temperature, where the changing curve of the mass of the rock sample with the drying temperature has an inflection point when the mobile fluids in the shale rock sample are removed completely, and a temperature corresponding to the inflection point is the target drying temperature $T_0$;

(5) setting 10 different drying times $t_1$, $t_2$, $t_3$, $t_4$, $t_5$, $t_6$, $t_7$, $t_8$, $t_9$ and $t_{10}$, which progressively increase in sequence by 2 h, where $t_5$ or $t_6$ is set to be identical to $t_0$ to reduce a testing workload under a condition of guaranteeing experimental accuracy;

(6) drying the shale rock sample 2 # according to a set time at the target drying temperature $T_0$, measuring corresponding rock sample masses $m'_1$, $m'_2$, $m'_3$, $m'_4$, $m'_5$, $m'_6$, $m'_7$, $m'_8$, $m'_9$ and $m'_{10}$ of the shale rock sample under different drying time conditions and carrying out a two-dimensional nuclear magnetic resonance test of the dried shale;

(7) plotting a changing curve of the mass of the shale rock sample 2 # with the drying time, where the mass of the rock sample does not change with the drying time when the mobile fluids in the shale rock sample are removed completely, and at this time, the corresponding time is the target drying time $t_0$; and (8) analyzing two-dimensional nuclear magnetic resonance spectra $T_1$ and $T_2$ after the target drying time $t_0$, and determining the final target drying temperature and drying time of the shale rock sample if the number of nuclear magnetic signals in minipores, mesopores and macropores does not change; and if the number of nuclear magnetic signals in minipores, mesopores and macropores in the two-dimensional nuclear magnetic resonance spectra $T_1$ and $T_2$ changes, reselecting rock samples and carrying out the experiment according to steps (1) to (7), and redetermining the target drying temperature $T_0$ and time $t_0$ of the shale rock sample;

B, a high pressure hg injection+injected fluid soaking+nuclear magnetic resonance test combined experiment of the shale rock sample (1) a high pressure hg injection test of the shale rock sample drying the prepared shale rock sample 4 # according to the determined target drying temperature $T_0$ and time $t_0$, performing the high pressure hg injection test on the dried rock sample, plotting a changing curve of a pore distribution frequency with a pore radius under a condition of semilogarithmic coordinates and determining a pore distribution characteristic of the shale rock sample; and (2) an injected fluid soaking+nuclear magnetic resonance test combined experiment of the shale rock sample;

C, processing and analysis of experimental data

1) Quantitative Evaluation on a Sensitivity of a Bedding Fracture Permeability of the Shale to an Injected Fluid (1) introducing a quantitative evaluation indicator for the sensitivity of the bedding fracture permeability to the injected fluid, as shown in formula (1):

$$R_K = \frac{K_a - K_b}{K_b} \cdot 100\% \qquad (1)$$

where $R_K$ represents a change rate of the bedding fracture permeability, %; $K_b$ represents the bedding fracture permeability of a dry shale rock sample, mD; and $K_a$ represents the bedding fracture permeability of the shale after being soaked in the injected fluid, mD;

(2) calculating the change rate of the bedding fracture permeability before and after the shale is soaked in the injected fluid according to the formula (1); and (3) quantitatively evaluating the sensitivity of the bedding fracture permeability of the shale to the injected fluid with reference to an evaluation indicator for a sensitivity influence degree in SY/T 5358-2010 "Formation damage evaluation by flow test";

2) Quantitative Evaluation on a Sensitivity of a Total Porosity of the Shale to an Injected Fluid (1) introducing a quantitative evaluation indicator for the sensitivity of the total porosity of the shale to the injected fluid, as shown in formula (2):

$$R_t = \frac{f_a - f_b}{f_b} \cdot 100\% \qquad (2)$$

where $R_t$ represents a change rate of the total porosity measured by a burden-pressure porosity and permeability meter, %; $f_b$ represents a porosity of the dry shale rock sample, %; and $f_a$ represents a porosity of the shale after being soaked in the injected fluid, %;

(2) calculating the change rate of the porosity before and after the shale is soaked in the injected fluid according to the formula (2); and (3) quantitatively evaluating the sensitivity of the total porosity of the shale to the injected fluid with reference to the evaluation indicator for a sensitivity influence degree in SY/T 5358-2010 "Formation damage evaluation by flow test";

3) Quantitative Evaluation on a Sensitivity of Pores of Different Sizes of the Shale to an Injected Fluid (1) calculation of a time-space conversion coefficient for a value of a nuclear magnetic resonance relaxation time $T_2$ and a pore size;

(2) establishment of a calibration relationship of the number of signals of a nuclear magnetic resonance $T_2$ spectrum to a saturated water porosity of the shale 1, calculating the saturated water porosity of the shale rock sample 5 # by a gravimetric method by the following calculation formula:

$$f_w = \left(\frac{m_w - m_0}{r_w}\right) \Big/ \left(\frac{pd^2 L}{4}\right) \cdot 100\% = \frac{4(m_w - m_0)}{r_w pd^2 L} \cdot 100\% \quad (3)$$

where $f_w$ represents the saturated water porosity, %; $m_w$ represents a weight of the rock sample after being saturated with water, g; $m_0$ represents a weight of the dried rock sample, g; $\rho_w$ represents the water density, g/cm³; d represents a diameter of the rock sample, cm; and L represents a length of the rock sample, cm;

2, testing a $T_2$ spectrum signal component based on nuclear magnetic resonance, and converting the nuclear magnetic $T_2$ spectrum signal component of the shale after being saturated with water into a porosity component according to formula (4):

$$f_{NMR,w}\big|_{T_2} = \frac{S_w f_w}{S_{ac,w} - S_{ac,d}} \quad (4)$$

where $f_{NMR,\ w}\big|_{T_2}$ represents a porosity component after saturation with water, %; $S_w$ represents a nuclear magnetic $T_2$ spectrum signal component after saturation with water, PU; $S_{ac,w}$ represents a cumulative value of nuclear magnetic $T_2$ spectrum signals after saturation with water, PU; and $S_{ac,d}$ represents a cumulative value of nuclear magnetic signals corresponding to the first peak of the $T_2$ spectrum of saturated water, PU;

3, based on a conversion principle of the nuclear magnetic $T_2$ spectrum signal component to the porosity component after saturation with water in step 2, converting the nuclear magnetic $T_2$ signal component after the shale is soaked in the injected fluid into the porosity component according to formula (5):

$$f_{NMR,s}\big|_{T_2} = \frac{S_s f_w}{S_{ac,w} - S_{ac,d}} \quad (5)$$

where $f_{NMR,\ s}\big|_{T_2}$ represents a porosity component after soaking the injected fluid, %; and $S_s$ represents a nuclear magnetic $T_2$ spectrum signal component after soaking in the injected fluid, PU; and 4, based on the porosity components obtained in steps 2 and 3, plotting a relationship curve of the porosity component and the cumulative value of porosity components changing with the relaxation time $T_2$ after the shale is saturated with water and soaked in the injected fluid, where the cumulative value of nuclear magnetic signals corresponding to the first peak in the $T_2$ spectrum needs to be removed from the curve;

(3) quantitative evaluation on a sensitivity of pores of different sizes to an injected fluid 1, based on the relationship curve of the cumulative value of porosity components changing with the relaxation time $T_2$, introducing quantitative evaluation indicators for the sensitivities of the total porosity of the shale and the porosities of different sizes, as shown in formulas (6), (7), (8), (9) and (10):

$$R_{NMR}^t = \frac{f_{NMR,s}^t - f_{NMR,w}^t}{f_{NMR,w}^t} \cdot 100\% \quad (6)$$

$$R_{NMR}^{mic} = \frac{f_{NMR,s}^{mic} - f_{NMR,w}^{mic}}{f_{NMR,w}^{mic}} \cdot 100\% \quad (7)$$

$$R_{NMR}^{min} = \frac{f_{NMR,s}^{min} - f_{NMR,w}^{min}}{f_{NMR,w}^{min}} \cdot 100\% \quad (8)$$

$$R_{NMR}^{mes} = \frac{f_{NMR,s}^{mes} - f_{NMR,w}^{mes}}{f_{NMR,w}^{mes}} \cdot 100\% \quad (9)$$

$$R_{NMR}^{mac} = \frac{f_{NMR,s}^{mac} - f_{NMR,w}^{mac}}{f_{NMR,w}^{mac}} \cdot 100\% \quad (10)$$

where $$R_{NMR}^t$$

represents a change rate of the total porosity calculated by a nuclear magnetic resonance method, %;

$$f_{NMR,s}^t$$

represents a cumulative value of total porosity components after soaking in the injected fluid, %;

$$f_{NMR,w}^t$$

represents a cumulative value of total porosity components after saturation with water, %;

$$R_{NMR}^{mic}$$

represents a change rate of a porosity of micropores, %;

$$f_{NMR,s}^{mic}$$

represents a cumulative value of porosity components of micropores after soaking in the injected fluid, %;

$$f_{NMR,w}^{mic}$$

represents a cumulative value of porosity components of micropores after saturation with water, %;

$$R_{NMR}^{min}$$

represents a change rate of a porosity of minipores, %;

$$f_{NMR,s}^{min}$$

represents a cumulative value of porosity components of minipores after soaking in the injected fluid, $$f_{NMR,w}^{min}$$

represents a cumulative value of porosity components of minipores after saturation with water, %;

$$R_{NMR}^{mes}$$

represents a change rate of a porosity of mesopores, %;

$$f_{NMR,s}^{mes}$$

represents a cumulative value of porosity components of mesopores after soaking in the injected fluid, %;

$$f_{NMR,w}^{mes}$$

represents a cumulative value of porosity components of mesopores after saturation with water, %;

$$R_{NMR}^{mac}$$

represents a change rate of a porosity of macropores, %;

$$f_{NMR,s}^{mac}$$

represents a cumulative value of porosity components of macropores after soaking in the injected fluid, %;

$$f_{NMR,w}^{mac}$$

represents a cumulative value of porosity components of macropores after saturation with water, %;

recommended classification criteria for pores of different sizes in a shale reservoir are as follows: pores having a radius of <0.01 μm are micropores, and 0.01 μm to 0.1 μm as minipores, 0.1 μm to 1.0 μm as mesopores, and >1.0 μm as macropores;

2, based on the time-space conversion coefficient k, calculating values of the relaxation time $T_2$ corresponding to divided radii of the micropores, minipores, mesopores and macropores, namely the values $T_{2, 10\,nm}$, $T_{2, 100\,nm}$ and $T_{2, 1000\,m}$ of the relaxation time $T_2$ corresponding to 10 nm, 100 nm and 1000 nm;

3, based on the values $T_{2, 10\,nm}$, $T_{2, 100\,nm}$ and $T_{2, 1000\,nm}$, calculating the porosities $$f_{NMR,w}^{mic}, f_{NMR,w}^{min}, f_{NMR,w}^{mes} \text{ and } f_{NMR,w}^{mac}$$

of the micropores, minipores, mesopores and macropores after saturation with water and the porosities $$f_{NMR,s}^{mic}, f_{NMR,s}^{min}, f_{NMR,s}^{mes}, \text{ and } f_{NMR,s}^{mac}$$

of the micropores, minipores, mesopores and macropores after soaking in the injected fluid by formulas (11) to (18):

$$f_{NMR,w}^{mic} = \frac{\left(S_w|_{T_{2,10\,nm}} - S_{ac,d}\right) \cdot f_w}{S_{ac,w} - S_{ac,d}} \quad (11)$$

$$f_{NMR,w}^{min} = \frac{\left(S_w|_{T_{2,100\,nm}} - S_w|_{T_{2,10\,nm}}\right) \cdot f_w}{S_{ac,w} - S_{ac,d}} \quad (12)$$

$$f_{NMR,w}^{mes} = \frac{\left(S_w|_{T_{2,1000\,nm}} - S_w|_{T_{2,100\,nm}}\right) \cdot f_w}{S_{ac,w} - S_{ac,d}} \quad (13)$$

$$f_{NMR,w}^{mac} = \frac{\left(S_{ac,w} - S_w|_{T_{2,1000\,nm}}\right) \cdot f_w}{S_{ac,w} - S_{ac,d}} \quad (14)$$

$$f_{NMR,s}^{mic} = \frac{\left(S_s|_{T_{2,10\,nm}} - S_{ac,d}\right) \cdot f_w}{S_{ac,w} - S_{ac,d}} \quad (15)$$

$$f_{NMR,s}^{min} = \frac{\left(S_a|_{T_{2,100\,nm}} - S_w|_{T_{2,10\,nm}}\right) \cdot f_w}{S_{ac,w} - S_{ac,d}} \quad (16)$$

$$f_{NMR,s}^{mes} = \frac{\left(S_s|_{T_{2,1000\,nm}} - S_s|_{T_{2,100\,nm}}\right) \cdot f_w}{S_{ac,w} - S_{ac,d}} \quad (17)$$

$$f_{NMR,s}^{mac} = \frac{\left(S_{ac,s} - S_s|_{T_{2,1000\,nm}}\right) \cdot f_w}{S_{ac,w} - S_{ac,d}} \quad (18)$$

where $S_w|_{T_{2, 10\,nm}}$ represents a cumulative value of nuclear magnetic $T_2$ spectrum signals of the micropores after saturation with water, PU; $S_w|_{T_{2, 100\,nm}}$ represents a cumulative value of nuclear magnetic $T_2$ spectrum signals of the minipores after saturation with water, PU; $S_w|_{T_{2, 1000\,nm}}$ represents a cumulative value of nuclear magnetic $T_2$ spectrum signals of the mesopores after saturation with water, PU; $S_s|_{T_{2, 10\,nm}}$ represents a cumulative value of nuclear magnetic $T_2$ spectrum signals of the micropores after soaking in the injected fluid, PU; $S_s|_{T_{2, 100\,nm}}$ represents a cumulative value of nuclear magnetic $T_2$ spectrum signals of the minipores after soaking in the injected fluid, PU; $S_s|_{T_{2, 1000\,nm}}$ represents a cumulative value of nuclear magnetic $T_2$ spectrum signals of the mesopores after soaking in the injected fluid, PU; $S_{ac,sd}$ represents a cumulative value of nuclear magnetic signals corresponding to the first peak of the $T_2$ spectrum after soaking in the injected fluid, PU; and $S_{ac,s}$ represents a cumulative value of nuclear magnetic signals of the $T_2$ spectrum after soaking in the injected fluid, PU; and 4, calculating the change rates of the total porosity and the porosities of different sizes before and after the shale rock sample is soaked in the injected fluid based on formulas (6), (7), (8), (9) and (10), and giving results of quantitative evaluation on the sensitivities of the total porosity and the pores of different sizes of the shale reservoir to the injected fluid with reference to the evaluation indicator for a sensitivity influence degree in SY/T 5358-2010 "Formation damage evaluation by flow test";

(III) Quantitative Evaluation on a Sensitivity of a Shale Matrix Permeability to an Injected Fluid where the quantitative evaluation on a sensitivity of a shale matrix permeability to an injected fluid includes the following steps:

1, sample preparation: selecting a shale rock sample from the same coring interval with the evaluation on the sensitivities of the porosity and the bedding fracture permeability to the injected fluid, and grinding the sample into 10/20-mesh particles with a mass of greater than 30 g;

2, drying the particle sample under the conditions of the target drying temperature $T_0$ and time $t_0$;

3, based on a pressure pulse decay principle, measuring a matrix permeability $K_{mb}$ of particles of the ground sample 6 # by using SMP-200 shale matrix permeameter;

4, placing the particle sample into a piston container, vacuumizing the piston container by using a vacuumizing pretreatment system for 48 h, and placing a sieve mesh on an upper portion of the piston container to protect the piston container;

5, placing a prepared injected fluid into another piston container, injecting the injected fluid into the piston container holding the particle sample by using ISCO pump to soak the particle sample for 48 h with a soaking pressure being identical to a formation pressure;

6, taking out the particle sample and drying the particle sample under the conditions of the target drying temperature $T_0$ and time $t_0$;

7, measuring the matrix permeability $K_{ma}$ of the particle sample after being soaked in the injected fluid by using the SMP-200 shale matrix permeameter;

8, calculating the change rate of the matrix permeability before and after the shale particle sample is soaked in the injected fluid based on formula (19):

$$R_{mK} = \frac{K_{ma} - K_{mb}}{K_{mb}} \cdot 100\% \tag{19}$$

where $R_{mK}$ represents the change rate of the matrix permeability of the shale particle sample, %; $K_{mb}$ represents the matrix permeability of the shale particle sample before being soaked in the injected fluid (after drying), mD; and $K_{ma}$ represents the matrix permeability of the shale particle sample after being soaked in the injected fluid, mD; and 9, giving a result of the quantitative evaluation on the sensitivity of the shale matrix permeability to the injected fluid with reference to the evaluation indicator for a sensitivity influence degree in SY/T 5358-2010 "Formation damage evaluation by flow test"; and giving a result of the quantitative evaluation on the sensitivity of the shale oil and gas reservoir to the injected fluid by comprehensive analysis based on changing laws of the total porosity, the porosities of different sizes, the bedding fracture permeability and the matrix permeability before and after the shale is soaked in the injected fluid.

The injected fluid soaking+nuclear magnetic resonance test combined experiment of the shale rock sample in step (2) of step B in the above solution may include the following steps:

1, drying the rock sample 5 # according to the determined target drying temperature $T_0$ and time $t_0$ and recording a length L, a diameter d and a mass $m_0$ thereof;

2, measuring the porosity $f_b$ and the bedding fracture permeability $K_b$ of the dried rock sample by using VINCI burden-pressure porosity and permeability meter;

3, placing the standard rock sample after the measurement of the porosity and the permeability into a core holder, loading a confining pressure of 2 MPa by using a hand pump, and then vacuumizing the rock sample by using the vacuumizing pretreatment system for 48 h;

4, preparing distilled water for the experiment and placing the distilled water into a piston container, and injecting the distilled water in the piston container into the rock sample at a constant pressure by using ISCO pump, where an injection pressure and the confining pressure progressively increase stepwise during a saturation process and a difference between the confining pressure and the injection pressure constant is kept at 2 MPa; when the injection pressure reaches the formation pressure, the saturation process is stopped; the saturation process of the rock sample is completed in a constant temperature box with a temperature being kept consistent with a formation temperature and a total saturation time of not less than 48 h;

5, taking the rock sample after being saturated with water out of the core holder and recording a mass $m_w$ thereof, testing the nuclear magnetic resonance $T_2$ spectrum of the rock sample after being saturated with water and continuously carrying out measurement for three times to reduce an experimental error;

6, drying the rock sample after being saturated with water in step 5 at the target drying temperature $T_0$ and time $t_0$;

7, placing the dried rock sample into the core holder, loading a confining pressure of 2 MPa by using the hand pump, and then vacuumizing the rock sample by using the vacuumizing pretreatment system for 48 h;

8, injecting the injected fluid in the piston container into the rock sample at a constant pressure by using the ISCO pump, where an injection pressure and the confining pressure progressively increase stepwise and a difference between the confining pressure and the injection pressure is kept constant at 2 MPa; when the injection pressure reaches the formation pressure, a saturation process is stopped and a total saturation time is not less than 48 h; the saturation process of the rock sample and the process of soaking the rock sample in the injected fluid are completed in the constant temperature box with a temperature being kept consistent with the formation temperature and a soaking time of 48 h;

9, carrying out a nuclear magnetic resonance $T_2$ spectrum test after the rock sample is soaked in the injected fluid, and continuously carrying out measurement for three times to reduce an experimental error;

10, drying the shale rock sample after being soaked in the injected fluid in step 9 at the target drying temperature $T_0$ and time $t_0$;

11, measuring the porosity $f_a$ and the permeability $K_a$ of the rock sample after being soaked in the injected fluid and dried by using the VINCI burden-pressure porosity and permeability meter; and 12, collating the experimental data.

The calculation of a time-space conversion coefficient for a value of a nuclear magnetic resonance relaxation time $T_2$ and a pore size in step (1) of step 3) of step C in the above solution may include the following steps:

1, extracting data of the nuclear magnetic resonance relaxation time $T_2$ and the number of nuclear magnetic signals after the rock sample 5 # is saturated with water, and plotting a changing curve of the number of nuclear magnetic signals with the relaxation time $T_2$ under the condition of semilogarithmic coordinates;

2, extracting data of the pore radius and the pore distribution frequency in results of the high pressure hg injection test, and plotting a changing curve of the pore distribution frequency with the pore radius under the condition of semilogarithmic coordinates;

3, integrating the curve data of steps 1 and 2 in a same coordinate system, and establishing a time-space conversion curve of nuclear magnetic resonance and high pressure hg injection, where an X-axis bottom coordinate represents the pore radius and a Y-axis principal coordinate represents the pore distribution frequency; an X-axis top coordinate represents the relaxation time $T_2$ and a Y-axis auxiliary coordinate represents the number of nuclear magnetic signals; and 4, calculating the time-space conversion coefficient starting from the relaxation time corresponding to a second peak because the first peak of the nuclear magnetic resonance $T_2$ spectrum after the shale rock sample is saturated with water represents organic matter signal display, and recording the values of the nuclear magnetic resonance relaxation time $T_{2i}$ and the pore radius $r_i$ when nuclear magnetic signal peaks correspond to pore distribution frequency peaks of high pressure hg injection one to one; and calculating the time-space conversion coefficient $k=(k_1+k_2+ \ldots +k_n)/n$ for the value of the nuclear magnetic resonance relaxation time $T_2$ and the pore size of the shale rock sample based on the above data, where n represents the number of peaks of the nuclear magnetic signal corresponding to the pore distribution frequency of high pressure hg injection.

The present disclosure has the following beneficial effects: the present disclosure innovatively provides a method for quantitative evaluation on a sensitivity of a shale oil and gas reservoir to injected fluids based on the nuclear magnetic resonance testing technology with two basic physical property parameters: porosity and permeability. The method solves the problems of the existing standard SY/T 5358-2010 "Formation damage evaluation by flow test", such as the failure to establish an effective driving system for a shale rock sample, a long experimental measurement time and a large error and a single evaluation indicator. The high pressure hg injection+injected fluid soaking+nuclear magnetic resonance test combined experiment method of the shale rock sample proposed in the present disclosure is capable of establishing a reservoir pressure and a temperature simulation condition conveniently and effectively and has the advantages of short experimental measurement period and high accuracy. Meanwhile, the present disclosure may give the results of quantitative evaluation on the sensitivities of the total porosity of the shale, pores of different sizes and matrix and bedding fracture permeabilities to injected fluids, respectively, and realizes quantitative and accurate evaluation on a sensitivity of a shale oil and gas reservoir to injected fluids.

The present disclosure provides a method for evaluation on a sensitivity of a shale oil and gas reservoir to injected fluids based on the nuclear magnetic resonance technology with two basic physical property parameters: porosity and permeability. The method realizes comprehensive and accurate evaluation on sensitivities of super tight shale oil and gas reservoirs to injected fluids and provides a brand-new scientific means for quantitative evaluation on sensitivities of the shale oil and gas reservoirs to the injected fluids.

DETAILED DESCRIPTION OF THE EMBODIMENTS

Figure 1A:
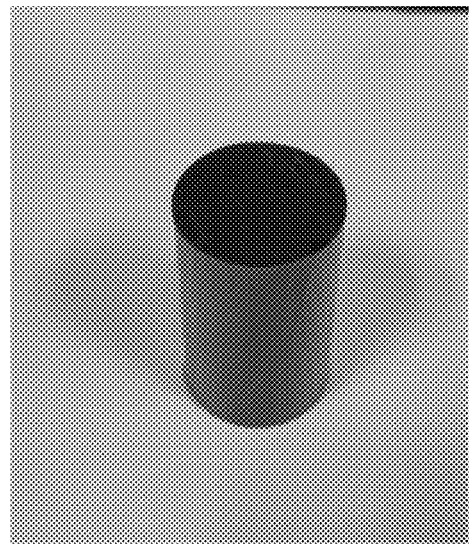
FIGS. 1A-F illustrate shale rock samples for experiments.
Figure 1B:
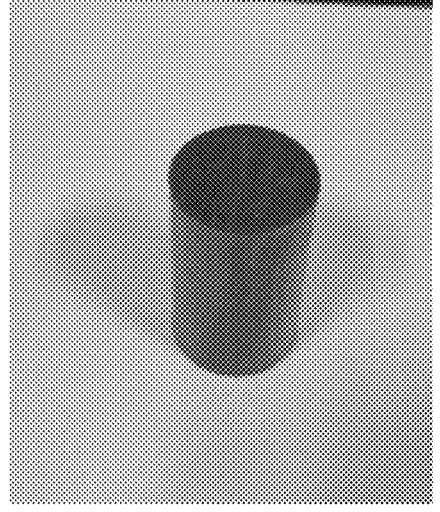
Figure 1C:
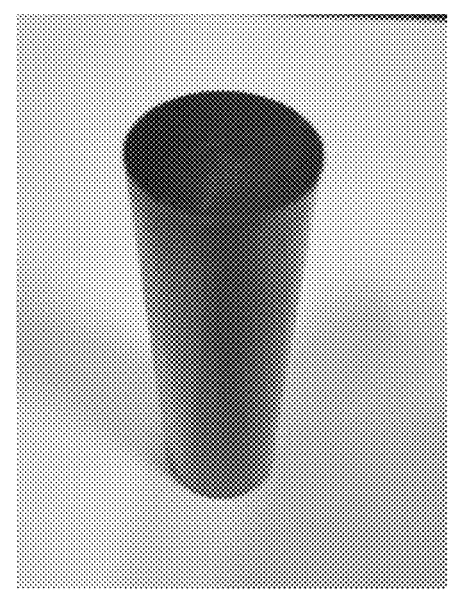
Figure 1D:
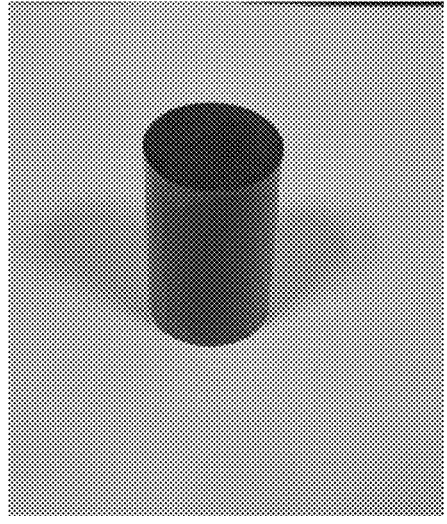
Figure 1E:
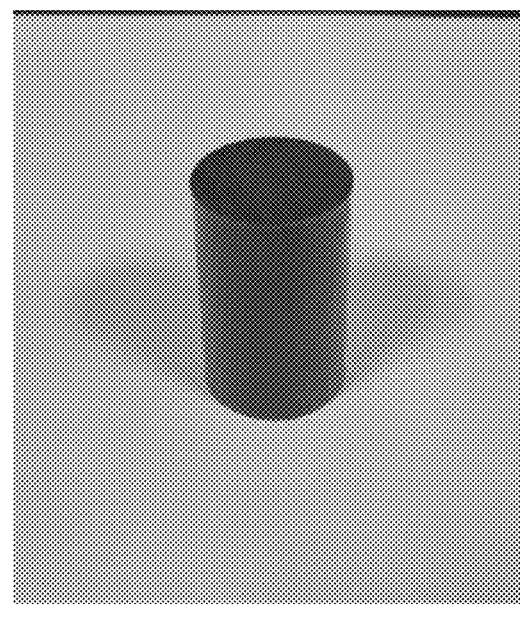
Figure 1F:
Figure 1F:

The present disclosure is further described below with reference to examples.

EXAMPLES

I, Preparation of Rock Samples

Three shale rock samples are selected from Qing1 interval of Qingshankou formation of Songliao basin and marked as 1 #, 2 # and 3 #. The rock samples 1 # and 2 # are used for determining a target drying temperature and time, and the rock sample 3 # is used for completing an evaluation experiment on sensitivities of a porosity and a permeability to an injected fluid. The rock sample 3 # is subjected to pretreatment before the experiment, and is cut into three small rock samples numbered as 4 #, 5 # and 6 #. The rock sample 4 # is used for a high pressure hg injection test. The rock sample 5 # is used for an evaluation experiment on sensitivities of a shale porosity and a bedding fracture permeability to an injected fluid. The rock sample 6 # is ground into 10/20-mesh particles for an evaluation experiment on a sensitivity of a shale matrix permeability. The shale rock samples for experiments are shown in FIGS. 1A-F.

II, Quantitative Evaluation on Sensitivities of a Shale Porosity and a Bedding Fracture Permeability to an Injected Fluid A, a target drying temperature and time of a shale rock sample are determined.

(1) Two shale rock samples are selected from Qing1 interval of Qingshankou formation and marked as 1 # and 2 #(see FIGS. TA-F).

(2) Drying temperatures are set at 50° C., 70° C., 90° C., 110° C., 130° C., 150° C., 170° C., 190° C., 210° C. and 230° C.

Figure 2:
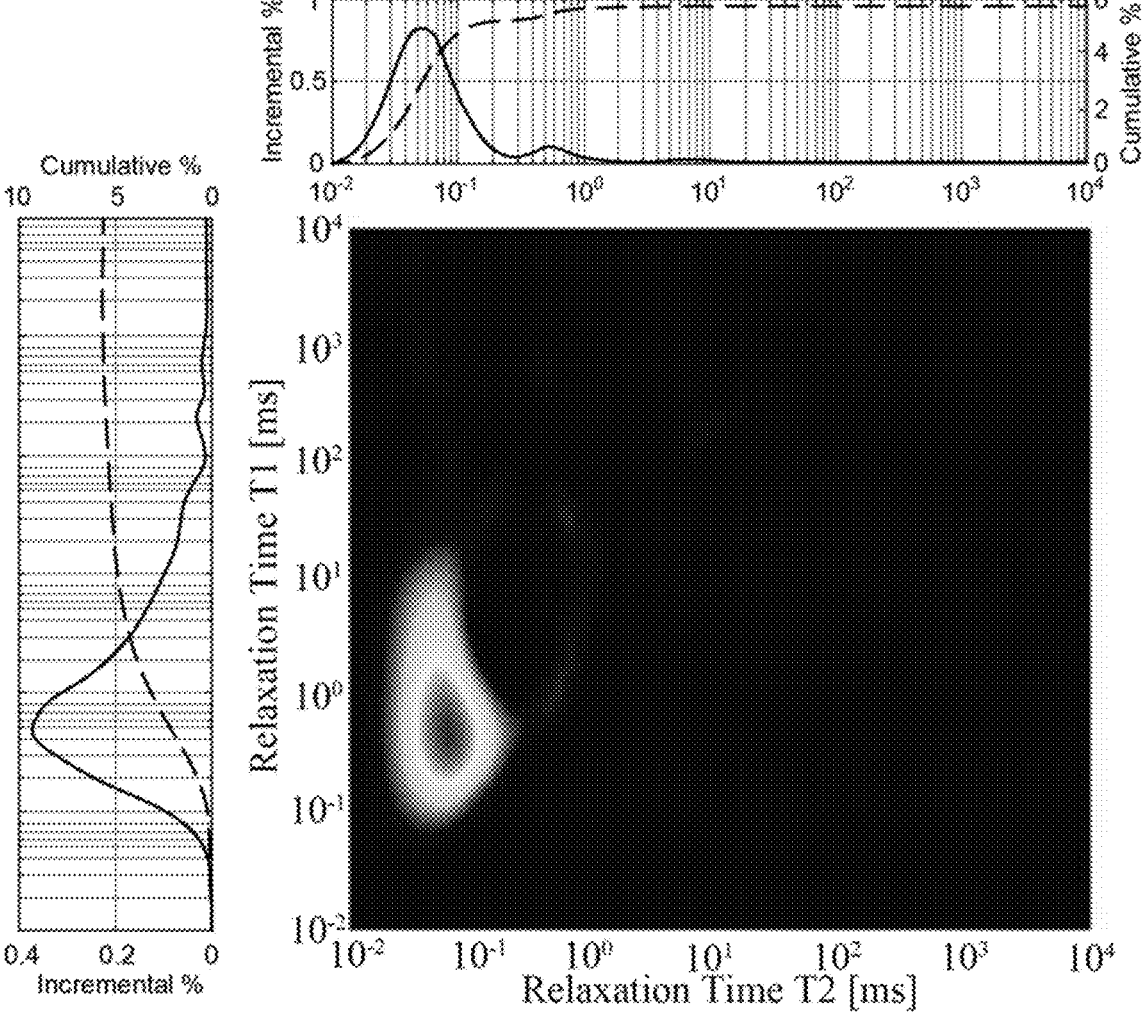
FIG. 2 illustrates a two-dimensional nuclear magnetic resonance test spectrum of a dried shale rock sample 1 #(with a drying temperature of 110° C. and a drying time of 8 h)

(3) The shale rock sample 1 # is dried at a set temperature condition for 8 h and corresponding rock sample masses thereof under different drying temperature conditions are measured, and a two-dimensional nuclear magnetic resonance test of the dried shale rock sample 1 # is carried out (see FIG. 2).

Figure 3:
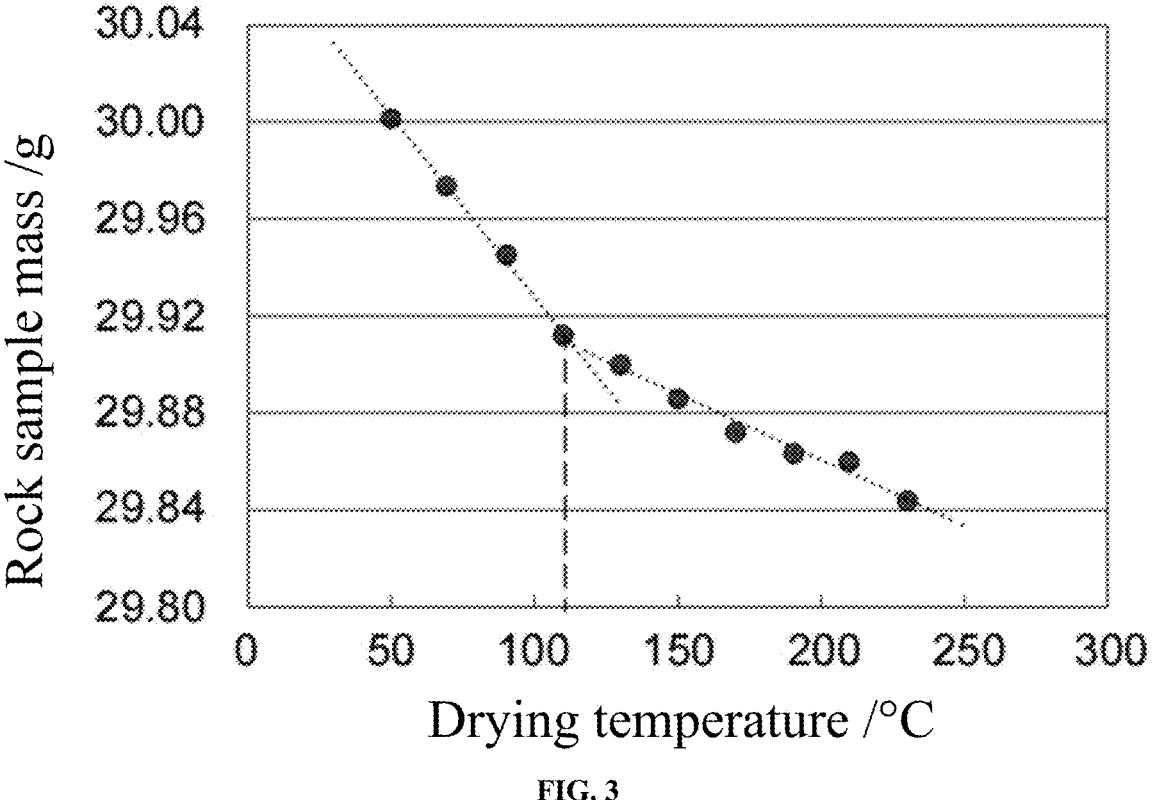
FIG. 3 illustrates a graph of a changing curve of the mass of the shale rock sample 1# with a drying temperature.

(4) A changing curve of the mass of the shale rock sample 1 # with a drying temperature is plotted (see FIG. 3). The changing curve of the mass of the rock sample with the drying temperature has an inflection point when the mobile fluids in the shale rock sample are removed completely, and a temperature corresponding to the inflection point is the target drying temperature $T_0=110°$ C.

(5) Drying times are set to be 2 h, 4 h, 6 h, 8 h, 10 h, 12 h, 14 h, 16 h, 18 h and 20 h.

Figure 4:
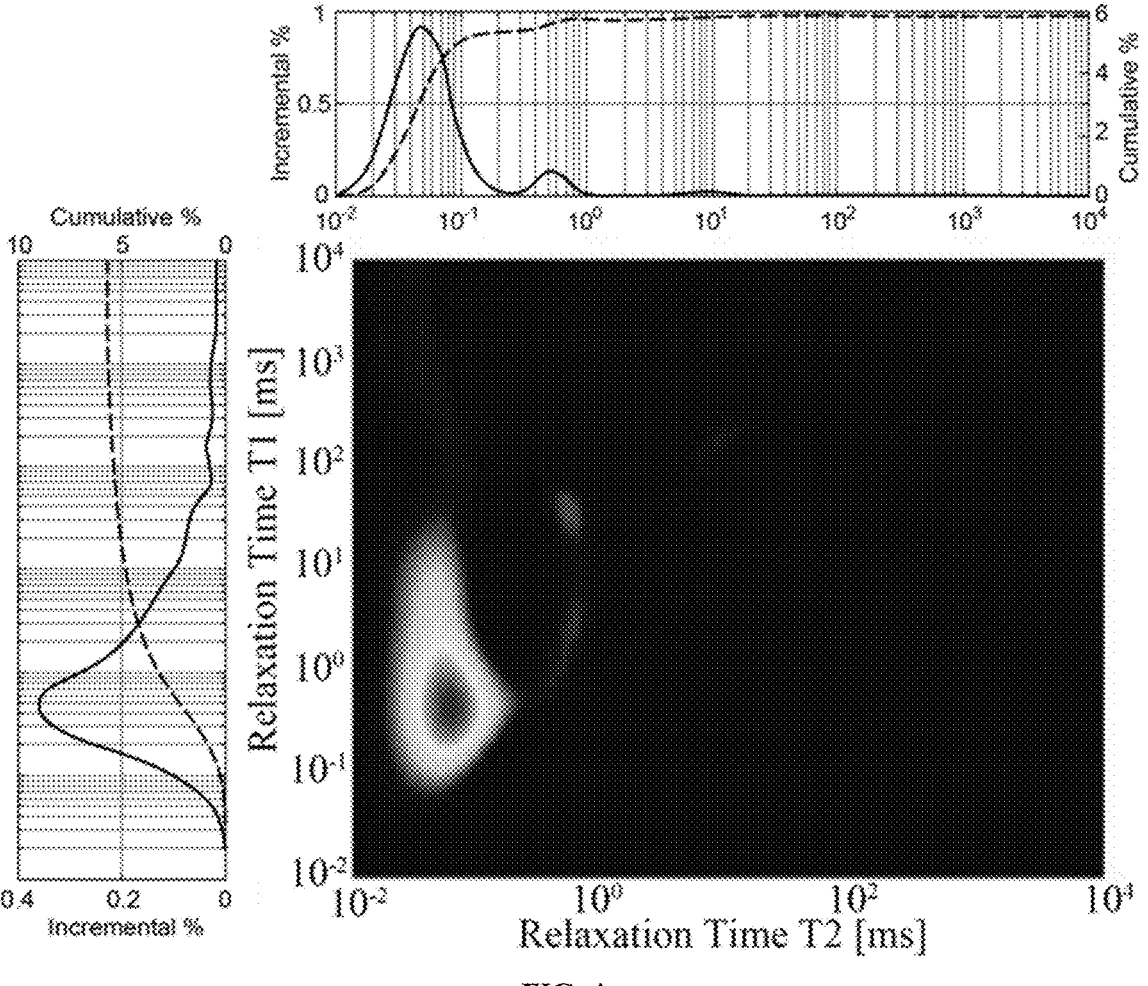
FIG. 4 shows a two-dimensional nuclear magnetic resonance test spectrum of a dried shale rock sample 2 #(with a drying temperature of 110° C. and a drying time of 10 h)

(6) The shale rock sample 2 # is dried according to a set time at the target drying temperature 110° C. and corresponding rock sample masses of the shale rock sample under different drying time conditions are measured, and a two-dimensional nuclear magnetic resonance test of the dried shale is carried out (see FIG. 4).

Figure 5:
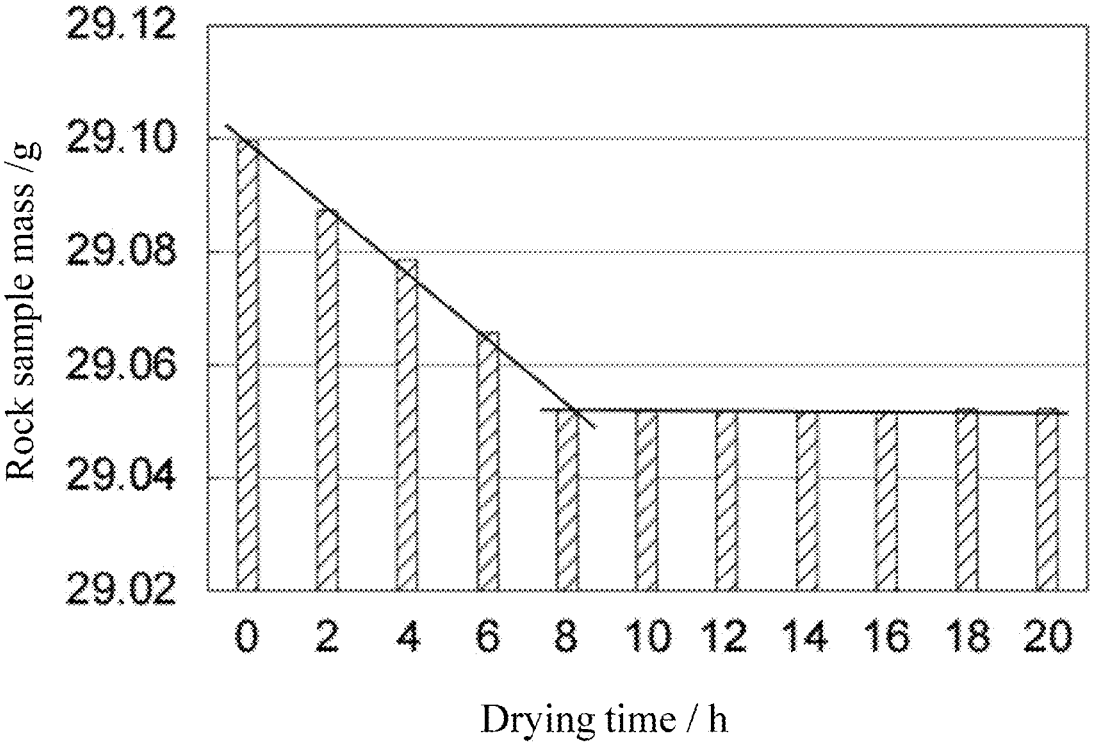
FIG. 5 illustrates a graph of a changing curve of the mass of the shale rock sample 2# with a drying time.

(7) A changing curve of the mass of the shale rock sample 2 # with a drying time is plotted (see FIG. 5). The mass of the rock sample does not change with the drying time when the mobile fluids in the shale rock sample are removed completely, and at this time, the corresponding time is the target drying time $t_0=8$ h.

(8) As can be seen from the contrastive analysis of FIG. 2 and FIG. 4, when the drying time is 10 h (longer than the target drying time 8 h), the number of nuclear magnetic signals in minipores, mesopores and macropores in two-dimensional nuclear magnetic resonance spectra $T_1$ and $T_2$ does not change, and the target drying temperature of the shale rock sample may be finally determined to be 110° C. and the drying time $t_0$ be 8 h.

B, a high pressure hg injection+injected fluid soaking+ nuclear magnetic resonance test combined experiment of the shale rock sample is carried out.

(1) A High Pressure Hg Injection Test of the Shale Rock Sample

The shale rock sample 4 # is dried at the temperature of 110° C. for 8 h and then the high pressure hg injection test is carried out. A changing curve of a pore distribution frequency with a pore radius is plotted under a condition of semilogarithmic coordinates (see FIG. 6), and a pore distribution characteristic of the shale rock sample is determined.

(2) An Injected Fluid Soaking+Nuclear Magnetic Resonance Test Combined Experiment of the Shale Rock Sample 1, the rock sample 5 # is dried at the temperature of 110° C. for 8 h, and a length L, a diameter d and a mass $m_0$ thereof are measured to be 3.02 cm, 2.50 cm and 35.0320 g, respectively.

2, a porosity $f_b$ and a bedding fracture permeability $K_b$ of the dried shale rock sample are measured by using VINCI burden-pressure porosity and permeability meter to be 6.854% and 0.184 mD, respectively.

3, the standard shale rock sample after the measurement of the porosity and the permeability is placed into a core holder, and a confining pressure of 2 MPa is loaded by using a hand pump. The rock sample is then vacuumized by using a vacuumizing pretreatment system for 48 h.

4, distilled water for the experiment is prepared and placed into a piston container, and the distilled water in the piston container is injected into the rock sample at a constant pressure by using ISCO pump. An injection pressure and the confining pressure progressively increase stepwise during a saturation process and a difference between the confining pressure and the injection pressure constant is kept at 2 MPa. When the injection pressure reaches a formation pressure of Qing1 interval, the saturation process is stopped. The saturation process of the rock sample is completed in a constant temperature box with a temperature being kept consistent with a formation temperature of Qing1 interval and a total saturation time of 48 h.

5, the rock sample after being saturated with water is taken out of the core holder, and a mass $m_w$ thereof is recorded, which is 35.8662 g. The nuclear magnetic resonance $T_2$ spectrum of the rock sample after being saturated with water is tested (see FIG. 6). The $T_2$ spectrum is an average value of three test results.

6, the shale rock sample after being saturated with water in step 5 is dried at the temperature of 110° C. for 8 h.

7, placing the dried rock sample into the core holder, loading a confining pressure of 2 MPa by using the hand pump, and then vacuumizing the rock sample by using the vacuumizing pretreatment system for 48 h;

8, the injected fluid (5% HCl) in the piston container is injected into the rock sample at a constant pressure by using the ISCO pump. An injection pressure and the confining pressure progressively increase stepwise and a difference between the confining pressure and the injection pressure is kept constant at 2 MPa. When the injection pressure reaches the formation pressure of Qing1 interval, a saturation process is stopped and a total saturation time is 48 h. The saturation process of the rock sample and the process of soaking the rock sample in the injected fluid (5% HCl) are completed in the constant temperature box with a temperature being kept consistent with the formation temperature of Qing1 interval and a soaking time of 48 h.

Figure 7:
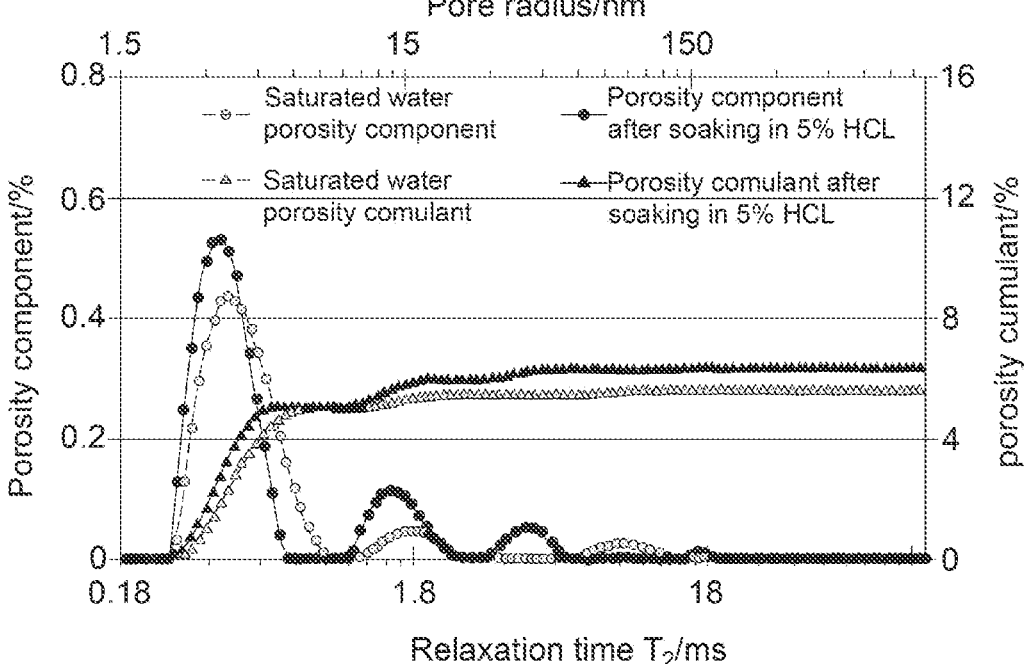
FIG. 7 illustrates a graph of a relationship curve of a porosity component and a cumulative value of porosity components changing with relaxation time $T_2$.

9, the nuclear magnetic resonance $T_2$ spectrum of the rock sample after being soaked in the injected fluid (5% HCl) is tested (see FIG. 7). It needs to be noted that the curve in FIG. 7 (the X-axis represents the relaxation time $T_2$ and the Y-axis represent a porosity component) represents the porosity component of the rock sample after being soaked in 5% HCl. The changing law of the nuclear magnetic signal component of the $T_2$ spectrum and the changing law of the porosity component are completely the same and differ in numerical value by one coefficient. Therefore, the $T_2$ spectrum after soaking in the injected fluid (5% HCl) is not given repeatedly.

10, the shale rock sample after being soaked in the injected fluid (5% HCl) in step 9 is dried at the temperature of 110° C. for 8 h.

11, the porosity $f_a$ and the permeability $K_a$ of the rock sample after being soaked in the injected fluid (5% HCl) and dried are measured by using the VINCI burden-pressure porosity and permeability meter to be 7.571% and 0.196 mD, respectively.

12, experimental data is collated.

C, processing and analysis of experimental data

1) Quantitative Evaluation on a Sensitivity of a Bedding Fracture Permeability of the Shale to an Injected Fluid (1) A quantitative evaluation indicator for the sensitivity of the bedding fracture permeability to an injected fluid is introduced, as shown in formula (1):

$$R_K = \frac{K_a - K_b}{K_b} \cdot 100\% \tag{1}$$

where $R_K$ represents a change rate of the bedding fracture permeability, %; $K_b$ represents the bedding fracture permeability of a dry shale rock sample, mD; and $K_a$ represents the bedding fracture permeability of the shale after being soaked in the injected fluid, mD.

(2) The change rate of the bedding fracture permeability before and after the shale is soaked in the injected fluid is calculated according to the formula (1): $K_b$=0.184 mD, $K_a$=0.196 mD, and $R_K$=6.52%.

(3) With reference to an evaluation indicator for a sensitivity influence degree in SY/T 5358-2010 "Formation damage evaluation by flow test" (see Table 1), the sensitivity of the bedding fracture permeability of the shale to the injected fluid (5% HCl) is evaluated as improved (weak), and the bedding fracture permeability of the shale after being soaked in 5% HCl is increased by 0.012 mD.

TABLE 1

| Evaluation Indicator for Sensitivity Influence Degree | |
| --- | --- |
| Change Rate Rk (%) | Sensitivity Influence Degree |
| $R_k \leq 5$ | Null |
| $5 < R_k \leq 30$ | Weak |
| $30 < R_k \leq 50$ | Below moderate |
| $50 < R_k \leq 70$ | Above moderate |
| $R_k \geq 70$ | Strong |

Notes: if $R_K$ is a "+" value, it represents an improvement; and if $R_K$ is a "−" value, it represents damage.

2) Quantitative Evaluation on a Sensitivity of a Total Porosity of the Shale to an Injected Fluid (1) A quantitative evaluation indicator for the sensitivity of the total porosity of the shale to the injected fluid is introduced, as shown in formula (2):

$$R_t = \frac{f_a - f_b}{R_b} \cdot 100\% \tag{2}$$

where $R_t$ represents a change rate of the total porosity measured by a burden-pressure porosity and permeability meter, %; $f_b$ represents a porosity of the dry shale rock sample, %; and $f_a$ represents a porosity of the shale after being soaked in the injected fluid, %.

(2) The change rate of the porosity before and after the shale is soaked in the injected fluid is calculated according to the formula (2): $f_b$=6.854%, $f_a$=7.571% and $R_t$=10.46%.

(3) With reference to the evaluation indicator for a sensitivity influence degree in SY/T 5358-2010 "Formation damage evaluation by flow test" (see Table 1), the sensitivity of the total porosity of the shale to the injected fluid (5% HCl) is evaluated as improved (weak), and the total porosity of the shale after being soaked in 5% HCl is increased by 0.717%.

Figure 6:
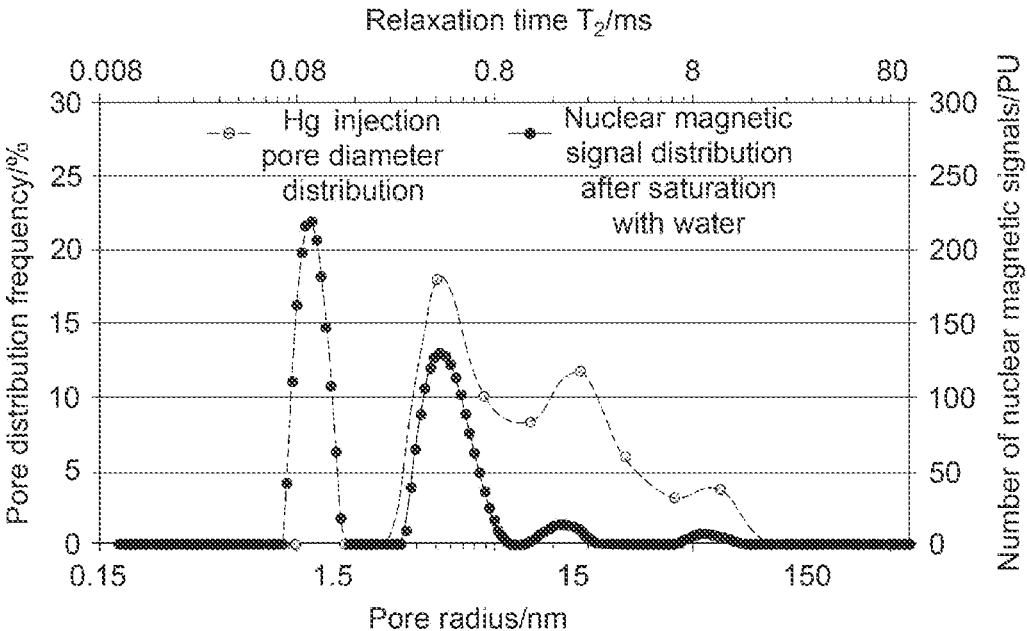
FIG. 6 illustrates a graph of a time-space conversion curve for a value of a nuclear magnetic resonance relaxation time $T_2$ and a pore size.

3) Quantitative Evaluation on a Sensitivity of Pores of Different Sizes of the Shale to an Injected Fluid (1) Calculation of a Time-Space Conversion Coefficient for a Value of a Nuclear Magnetic Resonance Relaxation Time $T_2$ and a Pore Size 1, data of the nuclear magnetic resonance relaxation time $T_2$ and the number of nuclear magnetic signals after the rock sample 5 # is saturated with water is extracted, and a changing curve of the number of nuclear magnetic signals with the relaxation time $T_2$ is plotted under the condition of semilogarithmic coordinates (see FIG. 6).

2, data of the pore radius and the pore distribution frequency in results of the high pressure hg injection test is extracted (see FIG. 6), and a changing curve of the pore distribution frequency with the pore radius (see FIG. 6) is plotted under the condition of semilogarithmic coordinates.

3, the curve data of steps 1 and 2 is integrated in a same coordinate system, and a time-space conversion curve of nuclear magnetic resonance and high pressure hg injection is established (see FIG. 6), where an X-axis bottom coordinate represents the pore radius and a Y-axis principal coordinate represents the pore distribution frequency; an X-axis top coordinate represents the relaxation time $T_2$ and a Y-axis auxiliary coordinate represents the number of nuclear magnetic signals.

4, the time-space conversion coefficient is calculated starting from the relaxation time corresponding to a second peak because the first peak of the nuclear magnetic resonance $T_2$ spectrum after the shale rock sample is saturated with water represents organic matter signal display, and the values of the nuclear magnetic resonance relaxation time $T_{2i}$ and the pore radius $r_i$ are recorded when nuclear magnetic signal peaks correspond to pore distribution frequency peaks of high pressure hg injection one to one (see Table 2). Based on the data of Table 2, the time-space conversion coefficient k=(9.49+9.00+7.07)/3 for the value of the nuclear magnetic resonance relaxation time $T_2$ and the pore size of the shale rock sample may be calculated as 8.52 nm/ms.

TABLE 2

| Contrast Data Table of Pore Radius and Relaxation Time | | |
| --- | --- | --- |
| r(nm) | $T_2$(ms) | k(nm/ms) |
| $r_1 = 4$ | $T_{21} = 0.4217$ | $k_1 = 9.49$ |
| $r_2 = 16$ | $T_{22} = 1.7783$ | $k_2 = 9.00$ |
| $r_3 = 63$ | $T_{23} = 8.9125$ | $k_3 = 7.07$ |

(2) Establishment of a Calibration Relationship of the Number of Signals of a Nuclear Magnetic Resonance $T_2$ Spectrum to a Saturated Water Porosity of the Shale 1, the saturated water porosity of the shale rock sample 5 # is calculated by a gravimetric method by the following calculation formula:

$$f_w = \left(\frac{m_w - m_0}{r_w}\right) \bigg/ \left(\frac{pd^2 L}{4}\right) \cdot 100\% = \frac{4(m_w - m_0)}{r_w pd^2 L} \cdot 100\% \tag{3}$$

where $f_w$ represents the saturated water porosity, %; $m_w$ represents a weight of the rock sample after being saturated with water, g; $m_0$ represents a weight of the dried rock sample, g; $\rho_w$ represents the water density, g/cm³; d represents a diameter of the rock sample, cm; and L represents a length of the rock sample, cm. The saturated water porosity of the shale rock sample $$5\# \text{ is } f_w = \frac{4 \cdot (35.8662 - 35.0320)}{1 \cdot 3.14 \cdot 2.5^2 \cdot 3.02} \cdot 100\% = 5.63\%.$$

2, a $T_2$ spectrum signal component is tested based on nuclear magnetic resonance, and the nuclear magnetic $T_2$ spectrum signal component of the shale after being saturated with water is converted into a porosity component according to formula (4):

$$f_{NMR,w}|_{T_2} = \frac{S_w f_w}{S_{ac,w} - S_{ac,d}} \quad (4)$$

where $f_{NMR,\,w}|_{T_2}$ represents a porosity component after saturation with water (see FIG. 7), %; $S_w$ represents a nuclear magnetic $T_2$ spectrum signal component after saturation with water, PU; $S_{ac,w}$ represents a cumulative value of nuclear magnetic $T_2$ spectrum signals after saturation with water, PU; and $S_{ac,d}$ represents a cumulative value of nuclear magnetic signals corresponding to the first peak of the $T_2$ spectrum of saturated water, PU.

Calculation is carried out according to the cumulative value of nuclear magnetic signals corresponding to the first peak of the $T_2$ spectrum in FIG. 6 to obtain: $S_{ac,d}$=1670.7 PU and $S_{ac,w}$=3349.1 PU.

3, based on a conversion principle of the nuclear magnetic $T_2$ spectrum signal component to the porosity component after saturation with water in step 2, the nuclear magnetic $T_2$ signal component after the shale is soaked in the injected fluid (5% HCl) is converted into the porosity component according to formula (5):

$$f_{NMR,s}|_{T_2} = \frac{S_s f_w}{S_{ac,w} - S_{ac,d}} \quad (5)$$

where $f_{NMR,\,s}|_{T_2}$ represents a porosity component after soaking in the injected fluid (see FIG. 7), %; and $S_s$ represents a nuclear magnetic $T_2$ spectrum signal component after soaking in the injected fluid (see FIG. 7), PU.

4, based on the porosity components obtained in steps 2 and 3, a relationship curve of the porosity component and the cumulative value of porosity components changing with the relaxation time $T_2$ after the shale is saturated with water and soaked in the injected fluid (5% HCl) (see FIG. 7) is plotted. It needs to be noted that the value of the porosity component contained in the first peak of nuclear magnetic resonance is removed from the porosity component curve in FIG. 7.

(3) Quantitative Evaluation on a Sensitivity of Pores of Different Sizes to an Injected Fluid 1, based on the relationship curve of the cumulative value of porosity components changing with the relaxation time $T_2$, quantitative evaluation indicators for the sensitivities of the total porosity of the shale and the porosities of different sizes are introduced, as shown in formulas (6), (7), (8), (9) and (10):

$$R_{NMR}^t = \frac{f_{NMR,s}^t - f_{NMR,w}^t}{f_{NMR,w}^t} \cdot 100\% \quad (6)$$

$$R_{NMR}^{mic} = \frac{f_{NMR,s}^{mic} - f_{NMR,w}^{mic}}{f_{NMR,w}^{mic}} \cdot 100\% \quad (7)$$

$$R_{NMR}^{min} = \frac{f_{NMR,s}^{min} - f_{NMR,w}^{min}}{f_{NMR,w}^{min}} \cdot 100\% \quad (8)$$

$$R_{NMR}^{mes} = \frac{f_{NMR,s}^{mes} - f_{NMR,w}^{mes}}{f_{NMR,w}^{mes}} \cdot 100\% \quad (9)$$

$$R_{NMR}^{mac} = \frac{f_{NMR,s}^{mac} - f_{NMR,w}^{mac}}{f_{NMR,w}^{mac}} \cdot 100\% \quad (10)$$

Where $$R_{NMR}^t$$

represents a change rate of the total porosity calculated by a nuclear magnetic resonance method, %;

$$f_{NMR,s}^t$$

represents a cumulative value of total porosity components after soaking in the injected fluid, %;

$$f_{NMR,w}^t$$

represents a cumulative value of total porosity components after saturation with water, %;

$$R_{NMR}^{mic}$$

represents a change rate of a porosity of micropores, %;

$$f_{NMR,s}^{mic}$$

represents a cumulative value of porosity components of micropores after soaking in the injected fluid, %;

$$f_{NMR,w}^{mic}$$

represents a cumulative value of porosity components of micropores after saturation with water, %;

$$R_{NMR}^{min}$$

represents a change rate of a porosity of minipores, %;

$$f_{NMR,s}^{min}$$

represents a cumulative value of porosity components of minipores after soaking in the injected fluid, $$f_{NMR,w}^{min}$$

represents a cumulative value of porosity components of minipores after saturation with water, %;

$$R_{NMR}^{mes}$$

represents a change rate of a porosity of mesopores, %;

$$f_{NMR,s}^{mes}$$

represents a cumulative value of porosity components of mesopores after soaking in the injected fluid, %;

$$f_{NMR,w}^{mes}$$

represents a cumulative value of porosity components of mesopores after saturation with water, %;

$$R_{NMR}^{mac}$$

represents a change rate of a porosity of macropores, %;

$$f_{NMR,s}^{mac}$$

represents a cumulative value of porosity components of macropores after soaking in the injected fluid, %;

$$f_{NMR,w}^{mac}$$

represents a cumulative value of porosity components of macropores after saturation with water, %.

It needs to be noted that recommended classification criteria for pores of different sizes in a shale reservoir are as follows: pores having a radius of <0.01 μm are micropores, and 0.01 μm to 0.1 μm as minipores, 0.1 μm to 1.0 μm as mesopores, and >1.0 μm as macropores.

2, based on the time-space conversion coefficient k, values of the relaxation time $T_2$ corresponding to divided radii of the micropores, minipores, mesopores and macropores are calculated, namely the values $T_{2,\,10\,nm}$, $T_{2,\,100\,nm}$ and $T_{2,\,1000\,nm}$ of the relaxation time $T_2$ corresponding to 10 nm, 100 nm and 1000 nm, namely, $$T_{2,10\,nm} = \frac{10\,nm}{8.52\,nm/ms} = 1.174\,ms,$$

$$T_{2,100\,nm} = \frac{100\,nm}{8.52\,nm/ms} = 11.74\,ms,\ and$$

$$T_{2,1000\,nm} = \frac{1000\,nm}{8.52\,nm/ms} = 117.4\,ms.$$

3, based on the values $T_{2,\,10\,nm}$, $T_{2,\,100\,nm}$ and $T_{2,\,1000\,nm}$, the porosities $$f_{NMR,w}^{mic},\ f_{NMR,w}^{min},\ f_{NMR,w}^{mes}\ and\ f_{NMR,w}^{mac}$$

of the micropores, minipores, mesopores and macropores after saturation with water and the porosities $$f_{NMR,s}^{mic},\ f_{NMR,s}^{min},\ f_{NMR,s}^{mes},\ and\ f_{NMR,s}^{mac}$$

of the micropores, minipores, mesopores and macropores after soaking in the injected fluid are calculated by formulas (11) to (18):

$$f_{NMR,w}^{mic} = \frac{\left(S_w|_{T_{2,10\,nm}} - S_{ac,d}\right) \cdot f_w}{S_{ac,w} - S_{ac,d}} \tag{11}$$

$$f_{NMR,w}^{min} = \frac{\left(S_w|_{T_{2,100\,nm}} - S_w|_{T_{2,10\,nm}}\right) \cdot f_w}{S_{ac,w} - S_{ac,d}} \tag{12}$$

$$f_{NMR,w}^{mes} = \frac{\left(S_w|_{T_{2,100\,nm}} - S_w|_{T_{2,10\,nm}}\right) \cdot f_w}{S_{ac,w} - S_{ac,d}} \tag{13}$$

$$f_{NMR,w}^{mac} = \frac{\left(S_{ac,w} - S_w|_{T_{2,1000\,nm}}\right) \cdot f_w}{S_{ac,w} - S_{ac,d}} \tag{14}$$

$$f_{NMR,s}^{mic} = \frac{\left(S_s|_{T_{2,10\,nm}} - S_{ac,sd}\right) \cdot f_w}{S_{ac,w} - S_{ac,d}} \tag{15}$$

$$f_{NMR,s}^{min} = \frac{\left(S_s|_{T_{2,100\,nm}} - S_s|_{T_{2,10\,nm}}\right) \cdot f_w}{S_{ac,w} - S_{ac,d}} \tag{16}$$

$$f_{NMR,s}^{mes} = \frac{\left(S_s|_{T_{2,1000\,nm}} - S_s|_{T_{2,100\,nm}}\right) \cdot f_w}{S_{ac,w} - S_{ac,d}} \tag{17}$$

$$f_{NMR,s}^{mac} = \frac{\left(S_{ac,s} - S_s|_{T_{2,1000\,nm}}\right) \cdot f_w}{S_{ac,w} - S_{ac,d}} \tag{18}$$

where $S_w|_{T_{2,\,10\,nm}}$ represents a cumulative value of nuclear magnetic $T_2$ spectrum signals of 2.10 nm the micropores after saturation with water, PU; $S_w|_{T_{2,\,100\,nm}}$ represents a cumulative value of nuclear magnetic $T_2$ spectrum signals of the minipores after saturation with water, PU; $S_w|_{T_{2,\,1000\,nm}}$ represents a cumulative value of nuclear magnetic $T_2$ Spectrum signals of the mesopores after saturation with water, PU; $S_s|_{T_{2,\,10\,nm}}$ represents a cumulative value of nuclear magnetic $T_2$ spectrum signals of the micropores after soaking in the injected fluid, PU; $S_s|_{T_{2,\,100\,nm}}$ represents a cumulative value of nuclear magnetic $T_2$ spectrum signals of the minipores after soaking in the injected fluid, PU; $S_s|_{T_{2,\,1000\,nm}}$ represents a cumulative value of nuclear magnetic $T_2$ spectrum signals of the mesopores after soaking in the injected fluid, PU; $S_{ac,sd}$ represents a cumulative value of nuclear magnetic signals corresponding to the first peak of the $T_2$ spectrum after soaking in the injected fluid, PU; and $S_{ac,s}$ represents a cumulative value of nuclear magnetic signals of the $T_2$ spectrum after soaking in the injected fluid, PU.

After being saturated with water, the porosity of the micropores is $$f_{NMR,w}^{mic} = 5.06\%,$$

and the porosity of the minipores $$f_{NMR,w}^{min} = 0.56\%,$$

the porosity of the mesopores $$f_{NMR,w}^{mes} = 0.01\%$$

and the porosity of the macropores $$f_{NMR,w}^{mac} = 0\%;$$

and after being soaked in the injected fluid (5% HCl), the porosity of the micropores is $$f_{NMR,s}^{mic} = 5.10\%,$$

and the porosity of the minipores $$f_{NMR,s}^{min} = 1.20\%,$$

the porosity of the mesopores $$f_{NMR,s}^{mes} = 0.02\%$$

and the porosity of the macropores $$f_{NMR,s}^{mac} = 0\%.$$

Taking $$f_{NMR,s}^{mic}$$

for example, the calculation process of the porosity of the micropores after being soaked in the injected fluid (5% HCl) is discussed in detail, and the calculation processes of the porosities of other different sizes are similar thereto, specifically shown as follows:

$$f_{NMR,s}^{mic} = \frac{\left(S_s\,|_{T_{2,10\,nm}} - S_{ac,sd}\right)\cdot f_w}{S_{ac,w} - S_{ac,d}} = \frac{(3255.54 - 1735.48)\cdot 5.63\%}{3349.1 - 1670.7} = 5.10\%.$$

4, the cumulative value of total porosity components after the shale rock sample 5 # is saturated with water is identical to the saturated water porosity, and hence $$f_{NMR,w}^t = f_w = 5.63\%.$$

As can be seen from FIG. 7, $$f_{NMR,s}^t = 6.32\%,$$

it can be known from the calculation of formula (6):

$$R_{NMR}^t = 12.26\%.$$

With reference to the evaluation indicator for a sensitivity influence degree in SY/T 5358-2010 "Formation damage evaluation by flow test" (see Table 1), the sensitivity of the total porosity of the shale to the injected fluid (5% HCl) is evaluated as improved (weak), and the total porosity of the shale after being soaked in 5% HCl calculated by the nuclear magnetic resonance method is increased by 0.69%.

The change rate of the porosities of different sizes before and after the shale rock sample is soaked in the injected fluid (5% HCl) is calculated based on formulas (7), (8), (9) and (10), and results (see Table 3) of quantitative evaluation on the sensitivities of the total porosity and the pores of different sizes of the shale reservoir to the injected fluid (5% HCl) are given with reference to the evaluation indicator for a sensitivity influence degree in SY/T 5358-2010 "Formation damage evaluation by flow test" (see Table 1).

TABLE 3

| | | | | |
|---|---|---|---|---|
| Results of Quantitative Evaluation on Sensitivities of Total Porosity and Pores of Different Sizes to Injected Fluid (5% HCl) | | | | |
| Pore Type | Saturated Water Porosity (%) | Porosity (%) after Damage by Injected Fluid (5% HCl) | Porosity Change Rate (%) | Result of Evaluation on Sensitivity |
| Micropores | 5.06 | 5.10 | 0.79 | Improved (no influence) |
| Minipores | 0.56 | 1.20 | 114.29 | Improved (strong) |
| Mesopores | 0.01 | 0.02 | 100.00 | Improved (strong) |
| Macropores | / | / | / | / |
| Total Pores | 5.63 | 6.32 | 12.26 | Improved (weak) |

III, Quantitative Evaluation on a Sensitivity of a Shale Matrix Permeability to an Injected Fluid The shale of Qing1 interval of Qingshankou formation of Songliao basin has a large quantity of micro-nano scale pores developing therein, and generally has a bedding fracture permeability of 0.001 mD and 0.1 mD and a matrix permeability of $10^{-9}$ mD to $10^{-4}$ mD. Evaluation on the sensitivity of the shale matrix permeability to the injected fluid by the traditional steady-state method in the standard SY/T5358-2010 "Formation damage evaluation by flow test" has no practical significance. It is specifically reflected in the following two aspects: (1) the shale matrix permeability is extremely low and a high displacing differential pressure and a long testing time are required to reach a steady flow state; and (2) the experimental data needs to be recorded manually during measurement with a large error. For the above two reasons, the present disclosure proposes a method for quantitative evaluation on a sensitivity of a shale matrix permeability to an injected fluid based on a non-steady-state method (pressure pulse decay).

The quantitative evaluation on a sensitivity of a shale matrix permeability to an injected fluid includes the following steps:

1, sample preparation A shale rock sample (rock sample 6 #) is selected from the same coring interval with the evaluation on the sensitivities of the porosity and the bedding fracture permeability to the injected fluid (5% HCl), and ground into 10/20-mesh particles, and 35 g of the particles is weighed.

2, the particle rock sample 6 # is dried at the temperature of 110° C. for 8 h.

3, based on a pressure pulse decay principle, a matrix permeability $K_b$ of particles of the ground sample 6 # is measured by using SMP-200 shale matrix permeameter.

4, the particle sample is placed into a piston container and vacuumized by using a vacuumizing pretreatment system for 48 h, and a sieve mesh is placed on an upper portion of the piston container to protect the piston container.

5, a prepared injected fluid (5% HCl) is placed into another piston container; and the injected fluid (5% HCl) is injected into the piston container holding the particle sample by using ISCO pump to soak the particle sample for 48 h with a soaking pressure being identical to the formation pressure of Qing interval.

6, the particle sample is taken out and dried at the temperature of 110° C. for 8 h.

7, the matrix permeability $K_m$ of the particle sample after being soaked in the injected fluid is measured by using the SMP-200 shale matrix permeameter.

8, the change rate of the matrix permeability before and after the shale particle sample is soaked in the injected fluid is calculated based on formula (19):

$$R_{mK} = \frac{K_{ma} - K_{mb}}{K_{mb}} \cdot 100\% \qquad (19)$$

where $R_{mK}$ represents the change rate of the matrix permeability of the shale particle sample, %; $K_{mb}$ represents the matrix permeability of the shale particle sample before being soaked in the injected fluid, mD; and $K_{ma}$ represents the matrix permeability of the shale particle sample after being soaked in the injected fluid, mD.

9, a result (see Table 4) of the quantitative evaluation on the sensitivity of the shale matrix permeability to the injected fluid (5% HCl) is given with reference to the evaluation indicator for a sensitivity influence degree in SY/T 5358-2010 "Formation damage evaluation by flow test" (see Table 1).

TABLE 4

| Result of Quantitative Evaluation on Sensitivity of Shale Matrix Permeability to Injected Fluid (5% HCl) | | | | |
|---|---|---|---|---|
| Sample Type | $K_{mb}$ (mD) | $K_{ma}$ (mD) | $R_{mK}$ (%) | Result of Evaluation on Sensitivity |
| Shale Matrix | $1.49 \times 10^{-4}$ | $3.68 \times 10^{-4}$ | 146.98 | Improved (strong) |

To sum up, the sensitivity of the total porosity of the shale to the injected fluid (5% HCl) is evaluated as improved (weak), and the bedding fracture permeability as improved (weak) and the matrix permeability as improved (strong); and the sensitivity of the shale rock sample for the experiment to the injected fluid (5% HCl) is evaluated by comprehensive analysis as improved (weak).

What is claimed is:

1. A method for quantitative evaluation on a sensitivity of a shale oil and gas reservoir to injected fluids, comprising:

(I) preparation of shale rock samples selecting three shale rock samples from a same coring interval and marking the three shale rock samples as 1 #, 2 # and 3 #, wherein the shale rock samples 1 # and 2 # are used for determining a target drying temperature and time, and the shale rock sample 3 # is used for completing an evaluation experiment on sensitivities of a shale porosity and a permeability to an injected fluid;

requirements for the shale rock sample 3 # are as follows:

the shale rock sample is a standard plunger sample having a diameter of 2.5 cm and a length of greater than or equal to 5 cm;

the shale rock sample 3 # is subjected to pretreatment before the evaluation experiment, and is cut into three small shale rock samples numbered as 4 #, 5 # and 6 #;

the shale rock sample 4 # is used for a high pressure mercury injection test;

the shale rock sample 5 # is used for evaluating sensitivities of the shale porosity and the bedding fracture permeability to the injected fluid; and the shale rock sample 6 # is ground into 10/20-mesh particles for evaluating a sensitivity of a shale matrix permeability;

(II) quantitative evaluation on the sensitivities of the shale porosity and the bedding fracture permeability to the injected fluid wherein a process of quantitative evaluation on the sensitivities of the shale porosity and the bedding fracture permeability to the injected fluid comprises three steps:

A, determination of the target drying temperature and time of the shale shock sample 1 # and the shale rock sample 2 # before conducting the evaluation experiment on the sensitivities of the shale porosity and the bedding fracture permeability to the injected fluid, removing mobile fluids comprising hydrocarbons and water existing in the shale rock samples to guarantee that the shale rock samples are clean;

(1) selecting two shale rock samples from a same coring interval and marking the shale rock samples as 1 # and 2 #;

(2) setting 10 different drying temperatures $T_{r1}$, $T_{r2}$, $T_{r3}$, $T_{r4}$, $T_{r5}$, $T_{r6}$, $T_{r7}$, $T_{r8}$, $T_{r9}$ and $T_{r10}$, which progressively increase in sequence by 20° C.;

(3) drying the shale rock sample 1 # at a set temperature condition for time to hours (h}, measuring corresponding rock sample masses $m_1$, $m_2$, $m_3$, $m_4$, $m_5$, $m_6$, $m_7$, $m_8$, $m_9$ and $m_{10}$ of the shale rock sample 1 #under different drying temperature conditions and carrying out a two-dimensional nuclear magnetic resonance test of the dried shale rock sample 1 # to obtain a two-dimensional nuclear magnetic resonance spectrum $T_1$;

(4) plotting a changing curve of the mass of the shale rock sample 1 # with the drying temperature, wherein the changing curve of the mass of the shale rock sample 1 # with the drying temperature has an inflection point when the mobile fluids in the shale rock sample 1 # are removed completely, and a temperature corresponding to the inflection point is the target drying temperature $T_0$;

(5) setting 10 different drying times $t_1$, $t_2$, $t_3$, $t_4$, $t_5$, $t_6$, $t_7$, $t_8$, $t_9$ and $t_{10}$, which progressively increase in sequence by 2 h, wherein $t_5$ or $t_6$ is set to be identical to $t_0$ to reduce a testing workload under a condition of guaranteeing experimental accuracy;

(6) drying the shale rock sample 2 # according to a set time at the target drying temperature $T_0$, measuring corresponding rock sample masses $m'_1$, $m'_2$, $m'_3$, $m'_4$, $m'_5$, $m'_6$, $m'_7$, $m'_8$, $m'_9$ and $m'_{10}$ of the shale rock sample 2 # under different drying time conditions and carrying out the two-dimensional nuclear magnetic resonance test of the dried shale rock sample 2 # to obtain a two-dimensional nuclear magnetic resonance spectrum $T_2$;

(7) plotting a changing curve of the mass of the shale rock sample 2 # with the drying time, wherein the mass of the shale rock sample 2 # does not change with the drying time when the mobile fluids in the shale rock sample 2 # are removed completely, and at this time, the corresponding time is the target drying time $t_0$; and (8) analyzing the two-dimensional nuclear magnetic resonance spectrum $T_1$ and the two-dimensional nuclear magnetic resonance spectrum $T_2$ after the target drying time $t_0$, and determining a final target drying temperature $T_0$ and drying time $t_0$ of the shale rock sample 1 # and the shale rock sample 2 # if the number of nuclear magnetic signals in minipores, mesopores and macropores does not change; and if a number of nuclear magnetic signals in minipores, mesopores and macropores in the two-dimensional nuclear magnetic resonance spectra $T_1$ and $T_2$ changes, reselecting the shale rock samples and carrying out the evaluation experiment according to steps (1) to (7), and redetermining the target drying temperature To and time to of the shale rock sample 1 # and the shale rock sample 2 #;

B, a high pressure mercury injection+injected fluid soaking+nuclear magnetic resonance test combined experiment (1) the high pressure mercury injection test of the shale rock sample 4 # drying the prepared shale rock sample 4 # according to the determined final target drying temperature $T_0$ and time $t_0$, performing the high pressure mercury injection test on the dried shale rock sample 4 #, plotting a changing curve of a pore distribution frequency with a pore radius under a condition of semilogarithmic coordinates and determining a pore distribution characteristic of the shale rock sample 4 #; and (2) an injected fluid soaking+nuclear magnetic resonance test combined experiment of the shale rock sample 5 #;

C, processing and analysis of experimental data 1) quantitative evaluation on the sensitivity of the bedding fracture permeability of the shale rock sample 5 # to the injected fluid (1) introducing a quantitative evaluation indicator for the sensitivity of the bedding fracture permeability to the injected fluid, as shown in formula (1):

$$R_K = \frac{K_a - K_b}{K_b} \times 100\% \qquad (1)$$

wherein $R_k$ represents a change rate of the bedding fracture permeability in units of percentage (%); $K_b$ represents the bedding fracture permeability of a dry shale rock sample in units of mD; and $K_a$ represents the bedding fracture permeability of the shale after being soaked in the injected fluid in units of mD;

(2) calculating the change rate of the bedding fracture permeability before and after the shale is soaked in the injected fluid according to the formula (1); and (3) quantitatively evaluating the sensitivity of the bedding fracture permeability of the shale rock sample 5 # to the injected fluid;

2) quantitative evaluation on a sensitivity of a total porosity of the shale to the injected fluid (1) introducing a quantitative evaluation indicator for the sensitivity of the total porosity of the shale to the injected fluid, as shown in formula (2):

$$R_t = \frac{f_a - f_b}{f_b} \cdot 100\% \qquad (2)$$

wherein $R_t$ represents a change rate of the total porosity measured by a burden-pressure porosity and permeability meter in units percentage (%); $f_b$ represents a porosity of the dry shale rock sample in units of percentage (%); and $f_a$ represents a porosity of the shale after being soaked in the injected fluid in units of percentage (%);

(2) calculating the change rate of the porosity before and after the shale is soaked in the injected fluid according to the formula (2); and (3) quantitatively evaluating the sensitivity of the total porosity of the shale to the injected fluid;

3) quantitative evaluation on a sensitivity of pores of different sizes of the shale to the injected fluid (1) calculation of a time-space conversion coefficient for a value of relaxation time of two-dimensional nuclear magnetic resonance spectrum $T_2$ and a pore size;

(2) establishment of a calibration relationship of the number of signals of the two-dimensional nuclear magnetic resonance spectrum $T_2$ to a saturated water porosity of the shale 1, calculating the saturated water porosity of the shale rock sample 5 # by a gravimetric method by the following calculation formula:

$$f_w = \left(\frac{m_w - m_0}{r_w}\right) \Big/ \left(\frac{pd^2 L}{4}\right) \cdot 100\% = \frac{4(m_w - m_0)}{r_w pd^2 L} \cdot 100\% \qquad (3)$$

wherein $f_w$ represents the saturated water porosity in units of percentage (%); $m_w$ represents a weight of the shale rock sample 5 # after being saturated with water in units of g; $m_0$ represents a weight of the dried shale rock sample 5 # in units of g; $r_w$ represents water density in units of g/cm$^3$; d represents a diameter of the shale rock sample 5 # in units of cm; and L represents a length of the shale rock sample 5 # in units of cm;

2, testing a $T_2$ spectrum signal component based on nuclear magnetic resonance, and converting the nuclear magnetic $T_2$ spectrum signal component of the shale after being saturated with water into a first porosity component according to formula (4):

$$f_{NMR,w}\,|_{T_2} = \frac{S_w f_w}{S_{ac,w} - S_{ac,d}} \qquad (4)$$

wherein $f_{NMR,\,w}|_{T2}$ represents the first porosity component after saturation with water in units of percentage (%); $S_w$ represents a nuclear magnetic $T_2$ spectrum signal component after saturation with water in units of PU; $S_{ac,w}$ represents a cumulative value of nuclear magnetic $T_2$ spectrum signals after saturation with water in units of PU; and $S_{ac,d}$ represents a cumulative value of nuclear magnetic signals corresponding to the first peak of the $T_2$ spectrum of saturated water in units of PU;

3, based on a conversion principle of the nuclear magnetic $T_2$ spectrum signal component to the porosity component after saturation with water in step 2, converting the nuclear magnetic $T_2$ spectrum signal component after the shale is soaked in the injected fluid into a second porosity component according to formula (5):

$$f_{NMR,s}\,|_{T_2} = \frac{S_s f_w}{S_{ac,w} - S_{ac,d}} \qquad (5)$$

wherein $f_{NMR,s}|_{T2}$ represents the second porosity component after soaking in the injected fluid in units of percentage (%; and $S_s$ represents a nuclear magnetic $T_2$ spectrum signal component after soaking in the injected fluid in units of PU; and 4, based on the first porosity component obtained in step 2 and the second porosity component obtained in step 3, plotting a relationship curve of the porosity component and a cumulative value of porosity components changing with the relaxation time $T_2$ after the shale is saturated with water and soaked in the injected fluid, wherein the cumulative value of nuclear magnetic signals corresponding to the first peak in the $T_2$ spectrum needs to be removed from the curve;

(3) quantitative evaluation on the sensitivity of pores of different sizes to the injected fluid 1, based on the relationship curve of the cumulative value of porosity components changing with the relaxation time $T_2$, introducing quantitative evaluation indicators for the sensitivities of the total porosity of the shale and the porosities of different sizes, as shown in formulas (6), (7), (8), (9) and (10):

$$R^t_{NMR} = \frac{f^t_{NMR,s} - f^t_{NMR,w}}{f^t_{NMR,w}} \cdot 100\% \qquad (6)$$

$$R^{mic}_{NMR} = \frac{F^{mic}_{NMR,s} - f^{mic}_{NMR,w}}{f^{mic}_{NMR,w}} \cdot 100\% \qquad (7)$$

-continued $$R^{min}_{NMR} = \frac{F^{min}_{NMR,s} - f^{min}_{NMR,w}}{f^{min}_{NMR,w}} \cdot 100\% \qquad (8)$$

$$R^{mes}_{NMR} = \frac{F^{mes}_{NMR,s} - f^{mes}_{NMR,w}}{f^{mes}_{NMR,w}} \cdot 100\% \qquad (9)$$

$$R^{mac}_{NMR} = \frac{f^{mac}_{NMR,s} - f^{mac}_{NMR,w}}{f^{mac}_{NMR,w}} \cdot 100\% \qquad (10)$$

wherein $R^t_{NMR}$ represents a change rate of the total porosity calculated by a nuclear magnetic resonance method in units of (%); $f^t_{NMR,\,s}$ represents a cumulative value of total porosity components after soaking in the injected fluid in units of percentage (%); $f^t_{NMR,\,w}$ represents a cumulative value of total porosity components after saturation with water in units of percentage (%); $R^{mic}_{NMR}$ represents a change rate of a porosity of micropores in units of percentage (%); $f^{mic}_{NMR,\,s}$ represents a cumulative value of porosity components of micropores after soaking in the injected fluid in units of percentage (%); $f^{mic}_{NMR,\,w}$ represents a cumulative value of porosity components of micropores after saturation with water in units of percentage (%); $R^{min}_{NMR}$ represents a change rate of a porosity of minipores in units of percentage (%); $f^{min}_{NMR,\,s}$ represents a cumulative value of porosity components of minipores after soaking in the injected fluid in units of percentage (%); $f^{min}_{NMR,\,w}$ represents a cumulative value of porosity components of minipores after saturation with water in units of percentage (%); $R^{mes}_{NMR}$ represents a change rate of a porosity of mesopores in units of percentage (%); $f^{mes}_{NMR,\,s}$ represents a cumulative value of porosity components of mesopores after soaking in the injected fluid in units of percentage (%); $f^{mes}_{NMR,\,w}$ represents a cumulative value of porosity components of mesopores after saturation with water in units of percentage (%); $R^{mac}_{NMR}$ represents a change rate of a porosity of macropores in units of percentage (%); $f^{mac}_{NMR,\,s}$ represents a cumulative value of porosity components of macropores after soaking in the injected fluid in units of percentage (%); $f^{mac}_{NMR,\,w}$ represents a cumulative value of porosity components of macropores after saturation with water in units of percentage (%);

recommended classification criteria for pores of different sizes in a shale reservoir are as follows: pores having a radius of <0.01 μm are micropores, and 0.01 μm to 0.1 μm as minipores, 0.1 μm to 1.0 μm as mesopores, and >1.0 μm as macropores;

2, based on the time-space conversion coefficient k, calculating values of the relaxation time $T_2$ corresponding to divided radii of the micropores, minipores, mesopores and macropores, namely the values $T_{2,\,10\,nm}$, $T_{2,\,100\,nm}$ and $T_{2,\,1000\,nm}$ of the relaxation time $T_2$ corresponding to 10 nm, 100 nm and 1000 nm;

3, based on the values T.sub.2.10 nm, T.sub.2,100 nm and T.sub.2, 1000 nm, calculating the porosities $f^{mic}_{NMR,\,w}$, $f^{min}_{NMR,\,w}$, $f^{mes}_{NMR,\,w}$ and $f^{mac}_{NMR,\,w}$ of the micropores, minipores, mesopores and macropores after saturation with water and the porosities $f^{mic}_{NMR,\,s}$, $f^{min}_{NMR,\,s}$, $f^{mes}_{NMR,\,s}$ and $f^{mac}_{NMR,\,s}$ of the micropores, minipores, mesopores and macropores after soaking in the injected fluid by formulas (11) to (18):

$$f^{mic}_{NMR,w} = \frac{\left(S_w\,|_{T_{2,10nm}} - S_{ac,d}\right) \cdot f_w}{S_{ac,w} - S_{ac,d}} \qquad (11)$$

-continued $$f_{NMR,w}^{min} = \frac{\left(S_w\,|_{T_{2,100\,nm}} - S_w\,|_{T_{2,10\,nm}}\right)\cdot f_w}{S_{ac,w} - S_{ac,d}} \qquad (12)$$

$$f_{NMR,w}^{mes} = \frac{\left(S_w\,|_{T_{2,1000\,nm}} - S_w\,|_{T_{2,100\,nm}}\right)\cdot f_w}{S_{ac,w} - S_{ac,d}} \qquad (13)$$

$$f_{NMR,w}^{mac} = \frac{\left(S_{ac,w} - S_w\,|_{T_{2,1000\,nm}}\right)\cdot f_w}{S_{ac,w} - S_{ac,d}} \qquad (14)$$

$$f_{NMR,s}^{mic} = \frac{\left(S_s\,|_{T_{2,10\,nm}} - S_{ac,sd}\right)\cdot f_w}{S_{ac,w} - S_{ac,d}} \qquad (15)$$

$$f_{NMR,s}^{min} = \frac{\left(S_s\,|_{T_{2,100\,nm}} - S_s\,|_{T_{2,10\,nm}}\right)\cdot f_w}{S_{ac,w} - S_{ac,d}} \qquad (16)$$

$$f_{NMR,s}^{mes} = \frac{\left(S_s\,|_{T_{2,1000\,nm}} - S_s\,|_{T_{2,100\,nm}}\right)\cdot f_w}{S_{ac,w} - S_{ac,d}} \qquad (17)$$

$$f_{NMR,s}^{mac} = \frac{\left(S_{ac,s} - S_s\,|_{T_{2,1000\,nm}}\right)\cdot f_w}{S_{ac,w} - S_{ac,d}} \qquad (18)$$

where in $S_w|T_{2,\,10\,nm}$ represents a cumulative value of nuclear magnetic $T_2$ spectrum signals of the micropores after saturation with water in units of PU; $S_w|T_{2,\,100\,nm}$ represents a cumulative value of nuclear magnetic $T_2$ spectrum signals of the minipores after saturation with water in units of PU; $S_w|T_{2,\,1000\,nm}$ represents a cumulative value of nuclear magnetic $T_2$ spectrum signals of the mesopores after saturation with water in units of PU; $S_s|T_{2,\,10\,nm}$ represents a cumulative value of nuclear magnetic $T_2$ spectrum signals of the micropores after soaking in the injected fluid in units of PU; $S_s|T_{2,\,100\,nm}$ represents a cumulative value of nuclear magnetic $T_2$ spectrum signals of the minipores after soaking in the injected fluid in units of PU; $S_s|T_{2,\,1000\,nm}$ represents a cumulative value of nuclear magnetic $T_2$ spectrum signals of the mesopores after soaking in the injected fluid in units of PU; $S_{ac,sd}$ represents a cumulative value of nuclear magnetic signals corresponding to the first peak of the $T_2$ spectrum after soaking in the injected fluid in units of PU; and $S_{ac,s}$ represents a cumulative value of nuclear magnetic signals of the $T_2$ spectrum after soaking in the injected fluid in units of PU; and 4, calculating the change rates of the total porosity and the porosities of different sizes before and after the shale rock sample is soaked in the injected fluid based on formulas (6), (7), (8), (9) and (10), and giving results of quantitative evaluation on the sensitivities of the total porosity and the pores of different sizes of the shale reservoir to the injected fluid;

(III) quantitative evaluation on the sensitivity of the shale matrix permeability to the injected fluid wherein the quantitative evaluation on the sensitivity of the shale matrix permeability to the injected fluid comprises the following steps:

1, sample preparation: selecting the shale rock sample 6 # from the same coring interval with the evaluation on the sensitivities of the porosity and the bedding fracture permeability to the injected fluid, and grinding the shale rock sample 6 #into a 10/20-mesh particles with a mass of greater than 30 g;

2, drying the particle under the conditions of the target drying temperature $T_0$ and time $t_0$;

3, based on a pressure pulse decay principle, measuring a matrix permeability $K_{mb}$ of particles of the ground sample 6 # by using a shale matrix permeameter;

4, placing the particle into a piston container, vacuumizing the piston container by using a vacuumizing pretreatment system for 48 h, and placing a sieve mesh on an upper portion of the piston container to protect the piston container;

5, placing the injected fluid into another piston container, injecting the injected fluid into the piston container holding the particle by using a pump to soak the particle sample for 48 h with a soaking pressure being identical to a formation pressure;

6, taking out the particle and drying the particle sample under the conditions of the target drying temperature $T_0$ and time $t_0$;

7, measuring the matrix permeability $K_{ma}$ of the particle after being soaked in the injected fluid by using the shale matrix permeameter;

8, calculating the change rate of the matrix permeability before and after the particle is soaked in the injected fluid based on formula (19):

$$R_{mK} = \frac{K_{ma} - K_{mb}}{K_{mb}} \times 100\% \qquad (19)$$

wherein $R_{mK}$ represents the change rate of the matrix permeability of the particle in units of percentage (%); $K_{mb}$ represents the matrix permeability of the particle after being soaked in the injected fluid (after drying) in units of mD; and $K_{ma}$ represents the matrix permeability of the particle after being soaked in the injected fluid in units of mD; and 9, giving a result of the quantitative evaluation on the sensitivity of the shale matrix permeability to the injected fluid; and giving a result of the quantitative evaluation on the sensitivity of the shale oil and gas reservoir to the injected fluid by comprehensive analysis based on changing laws of the total porosity, the porosities of different sizes, the bedding fracture permeability and the matrix permeability before and after the shale is soaked in the injected fluid.

2. The method for quantitative evaluation on the sensitivity of the shale oil and gas reservoir to injected fluids according to claim 1, wherein the injected fluid soaking+nuclear magnetic resonance test combined experiment of the shale rock sample 5 # in step (2) of step B comprise:

1, drying the shale rock sample 5 #according to the determined final target drying temperature $T_0$ and time $t_0$ and recording a length L, a diameter d and a mass $m_0$ thereof;

2, measuring the porosity $f_b$ and the bedding fracture permeability $K_b$ of the dried rock sample 5 # by using the burden-pressure porosity and permeability meter;

3, placing the shale rock sample 5 # after the measurement of the porosity and the permeability into a core holder, loading a confining pressure of 2 MPa by using a hand pump, and then vacuumizing the shale rock sample 5 # by using the vacuumizing pretreatment system for 48 h;

4, preparing distilled water for the experiment and placing the distilled water into a piston container, and injecting the distilled water in the piston container into the rock sample at a constant pressure by using the pump, wherein an injection pressure and the confining pressure progressively increase stepwise during a saturation process and a difference between the confining pressure and the injection pressure constant is kept at 2 MPa;

when the injection pressure reaches the formation pressure, the saturation process is stopped;

the saturation process of the rock sample is completed in a constant temperature box with a temperature being kept consistent with a formation temperature and a total saturation time of not less than 48 h;

5, taking the shale rock sample 5 # after being saturated with water out of the core holder and recording a mass $m_w$ thereof, testing the nuclear magnetic resonance $T_2$ spectrum of the shale rock sample 5 # after being saturated with water and continuously carrying out measurement for three times to reduce an experimental error;

6, drying the shale rock sample 5 # after being saturated with water in step 5 at the target drying temperature $T_0$ and time $t_0$;

7, placing the dried shale rock sample 5 #into the core holder, loading the confining pressure of 2 MPa by using the hand pump, and then vacuumizing the shale rock sample 5 # by using the vacuumizing pretreatment system for 48 h;

8, injecting the injected fluid in the piston container into the shale rock sample 5 # at the constant pressure by using the pump, wherein the injection pressure and the confining pressure progressively increase stepwise and the difference between the confining pressure and the injection pressure is kept constant at 2 MPa;

when the injection pressure reaches the formation pressure, the saturation process is stopped and the total saturation time is not less than 48 h; the saturation process of the rock sample and the process of soaking the rock sample in the injected fluid are completed in the constant temperature box with the temperature being kept consistent with the formation temperature and a soaking time of 48 h;

9, carrying out a nuclear magnetic resonance $T_2$ spectrum test after the shale rock sample 5 # is soaked in the injected fluid, and continuously carrying out measurement for three times to reduce an experimental error;

10, drying the shale rock sample 5 # after being soaked in the injected fluid in step 9 at the target drying temperature To and time to;

11, measuring the porosity $f_a$ and the permeability $K_a$ of the rock sample after being soaked in the injected fluid and dried by using the burden-pressure porosity and permeability meter; and 12, collating experimental data.

3. The method for quantitative evaluation on the sensitivity of the shale oil and gas reservoir to injected fluids according to claim 1, wherein the calculation of the time-space conversion coefficient for the value of the nuclear magnetic resonance relaxation time $T_2$ and the pore size in step (1) of step 3) of step C comprises:

1, extracting data of the nuclear magnetic resonance relaxation time $T_2$ and the number of nuclear magnetic signals after the shale rock sample 5 # is saturated with water, and plotting a changing curve of the number of nuclear magnetic signals with the relaxation time $T_2$ under the condition of semilogarithmic coordinates;

2, extracting data of the pore radius and the pore distribution frequency in results of the high pressure mercury injection test, and plotting a changing curve of the pore distribution frequency with the pore radius under the condition of semilogarithmic coordinates;

3, integrating the curve data of steps 1 and 2 in a same coordinate system, and establishing a time-space conversion curve of nuclear magnetic resonance and high pressure mercury injection, wherein an X-axis bottom coordinate represents the pore radius and a Y-axis principal coordinate represents the pore distribution frequency; an X-axis top coordinate represents the relaxation time $T_2$ and a Y-axis auxiliary coordinate represents the number of nuclear magnetic signals; and 4, calculating the time-space conversion coefficient starting from the relaxation time corresponding to a second peak because the first peak of the nuclear magnetic resonance $T_2$ spectrum after the shale rock sample 5 # is saturated with water represents organic matter signal display, and recording the values of the nuclear magnetic resonance relaxation time $T_{2i}$ and the pore radius $r_i$ when nuclear magnetic signal peaks correspond to pore distribution frequency peaks of high pressure mercury injection one to one; and calculating the time-space conversion coefficient $k=(k_1+k_2+ \ldots +k_n)/n$ for the value of the nuclear magnetic resonance relaxation time $T_2$ and the pore size of the shale rock sample 5 #based on the above data, wherein n represents the number of peaks of the nuclear magnetic signal corresponding to the pore distribution frequency of high pressure mercury injection.

* * * * *